(12) United States Patent
Varona et al.

(10) Patent No.: US 12,239,748 B2
(45) Date of Patent: Mar. 4, 2025

(54) ABSORBENT MATERIAL, AND SYSTEM AND METHOD OF MAKING SAME

(71) Applicant: DSG TECHNOLOGY HOLDINGS LTD., Kwai Chung (HK)

(72) Inventors: Eugenio Varona, Marietta, GA (US); Andrew Wright, Rotherham (GB); Dennis Smid, Wolvega (NL)

(73) Assignee: DSG Technology Holdings LTD., Kwai Chung (HK)

( * ) Notice: Subject to any disclaimer, the term of this patent is extended or adjusted under 35 U.S.C. 154(b) by 546 days.

(21) Appl. No.: 17/307,424

(22) Filed: May 4, 2021

(65) Prior Publication Data

US 2021/0322623 A1   Oct. 21, 2021

Related U.S. Application Data

(63) Continuation of application No. 15/905,813, filed on Feb. 26, 2018, now Pat. No. 11,027,039.

(60) Provisional application No. 62/482,277, filed on Apr. 6, 2017, provisional application No. 62/463,714, filed on Feb. 26, 2017.

(51) Int. Cl.
| | |
|---|---|
| *B01J 20/24* | (2006.01) |
| *A61F 13/531* | (2006.01) |
| *A61L 15/22* | (2006.01) |
| *A61L 15/60* | (2006.01) |
| *B01J 20/26* | (2006.01) |
| *B01J 20/28* | (2006.01) |
| *B01J 20/30* | (2006.01) |
| *B01J 20/32* | (2006.01) |
| *A61F 13/53* | (2006.01) |

(52) U.S. Cl.
CPC ............ *A61L 15/60* (2013.01); *A61F 13/531* (2013.01); *A61L 15/225* (2013.01); *B01J 20/24* (2013.01); *B01J 20/267* (2013.01); *B01J 20/28028* (2013.01); *B01J 20/3085* (2013.01); *B01J 20/3208* (2013.01); *B01J 20/3295* (2013.01); *A61F 2013/530343* (2013.01); *A61F 2013/530613* (2013.01)

(58) Field of Classification Search
CPC ...... A61L 15/60; A61F 13/531; A61L 15/225; A61F 2013/530343; A61F 2013/530613; B01J 20/24; B01J 20/267; B01J 20/28028; B01J 20/3085; B01J 20/3208; B01J 20/3295
USPC ........................................................ 604/374
See application file for complete search history.

(56) References Cited

U.S. PATENT DOCUMENTS

| | | | |
|---|---|---|---|
| 3,661,154 A | 5/1972 | Torr | |
| 5,002,814 A * | 3/1991 | Knack | ..................... A61L 15/60 |
| | | | 428/6 |
| 5,300,192 A | 4/1994 | Hansen et al. | |
| 5,432,000 A | 7/1995 | Young, Sr. et al. | |
| 5,516,585 A | 5/1996 | Young, Sr. et al. | |
| 6,387,495 B1 | 5/2002 | Reeves et al. | |
| 6,533,978 B1 | 3/2003 | Wisneski et al. | |
| 6,720,073 B2 | 4/2004 | Lange et al. | |
| 6,794,557 B1 | 9/2004 | Klemp et al. | |
| 7,381,294 B2 | 6/2008 | Suzuki et al. | |
| 8,372,320 B2 | 2/2013 | Gardner et al. | |
| 8,802,786 B2 | 8/2014 | Shi et al. | |
| 2003/0111774 A1 | 6/2003 | Kellenberger et al. | |
| 2004/0193128 A1 | 9/2004 | Klemp et al. | |
| 2004/0193218 A1 | 9/2004 | Butler | |
| 2005/0129846 A1 | 6/2005 | Reeves et al. | |
| 2006/0040579 A1 | 2/2006 | Sheldon et al. | |
| 2011/0172507 A1* | 7/2011 | Lademann | ............... A61L 15/56 |
| | | | 604/372 |
| 2012/0267570 A1 | 10/2012 | Shi et al. | |
| 2013/0260988 A1 | 10/2013 | Herfert et al. | |
| 2014/0276518 A1 | 9/2014 | Varona et al. | |
| 2014/0303582 A1 | 10/2014 | Wright et al. | |
| 2015/0045756 A1 | 2/2015 | Wright et al. | |
| 2016/0243522 A1 | 8/2016 | Rottger et al. | |

FOREIGN PATENT DOCUMENTS

| | | | | |
|---|---|---|---|---|
| CN | 1348388 A | 5/2002 | | |
| CN | 103547603 A | 1/2014 | | |
| CN | 105916473 A | 8/2016 | | |
| EP | 0947549 A1 | 10/1999 | | |
| EP | 1072244 B1 * | 9/2004 | ............. | A61F 13/53 |
| JP | S6363723 A | 3/1988 | | |
| JP | S63159560 A | 7/1988 | | |
| JP | H10168230 A | 6/1998 | | |
| JP | H1193073 A | 4/1999 | | |
| JP | 2008237430 A | 10/2008 | | |
| JP | 2016521143 A | 7/2016 | | |

(Continued)

OTHER PUBLICATIONS

Extended EP Search Report, issued in EP Application No. 18757335.7 dated Dec. 3, 2020 [10 pages].

(Continued)

*Primary Examiner* — Edward M Johnson
(74) *Attorney, Agent, or Firm* — Alberto Q. Amatong, Jr.; Amatong McCoy LLC

(57) ABSTRACT

A fiber-SAP particle includes a superabsorbent core particle (SAP core particle) and a plurality of fibers attached to the SAP core particle and extending therefrom. The fiber-SAP particles may be formed in a fluidized bed chamber using a spray drying process. The fiber-SAP particles may be incorporated into absorbent cores and articles, such as in disposable diapers.

32 Claims, 14 Drawing Sheets

(56) References Cited

FOREIGN PATENT DOCUMENTS

| KR | 20160037835 A | 4/2016 | | |
| WO | 03057764 A2 | 7/2003 | | |
| WO | WO-2006020213 A2 * | 2/2006 | ....... | A61F 13/00042 |
| WO | WO-2014050366 A1 * | 4/2014 | ......... | A61F 13/4756 |
| WO | 2014145326 A1 | 9/2014 | | |

OTHER PUBLICATIONS

International Preliminary Report on Patentability issued in PCT Application No. PCT/US2018/019790, mailed Sep. 16, 2019 [27 pages].

International Search Report Issued Jul. 30, 2018, during the prosecution of International Application No. PCT/US2018/019790. [5 pages].

Momen, Ayyoub M.; Ultrasonic Clothes Dryer; PowerPoint presentation; 2016; pp. 1-17; Oak Ridge National Laboratory; U.S. Department of Energy.

Nechita, P.; Panaitescu, D.M.; Improving the Dispersibility of Cellulose Microfibrillated Structures in Polymer Matrix by Controlling Drying Conditions and Chemical Surface Modifications; Cellulose Chemistry and Technology; 2013; pp. 711-719; vol. 47 (9-10).

Written Opinion Issued Jul. 30, 2018, during the prosecution of International Application No. PCT/US2018/019790. [14 pages].

* cited by examiner

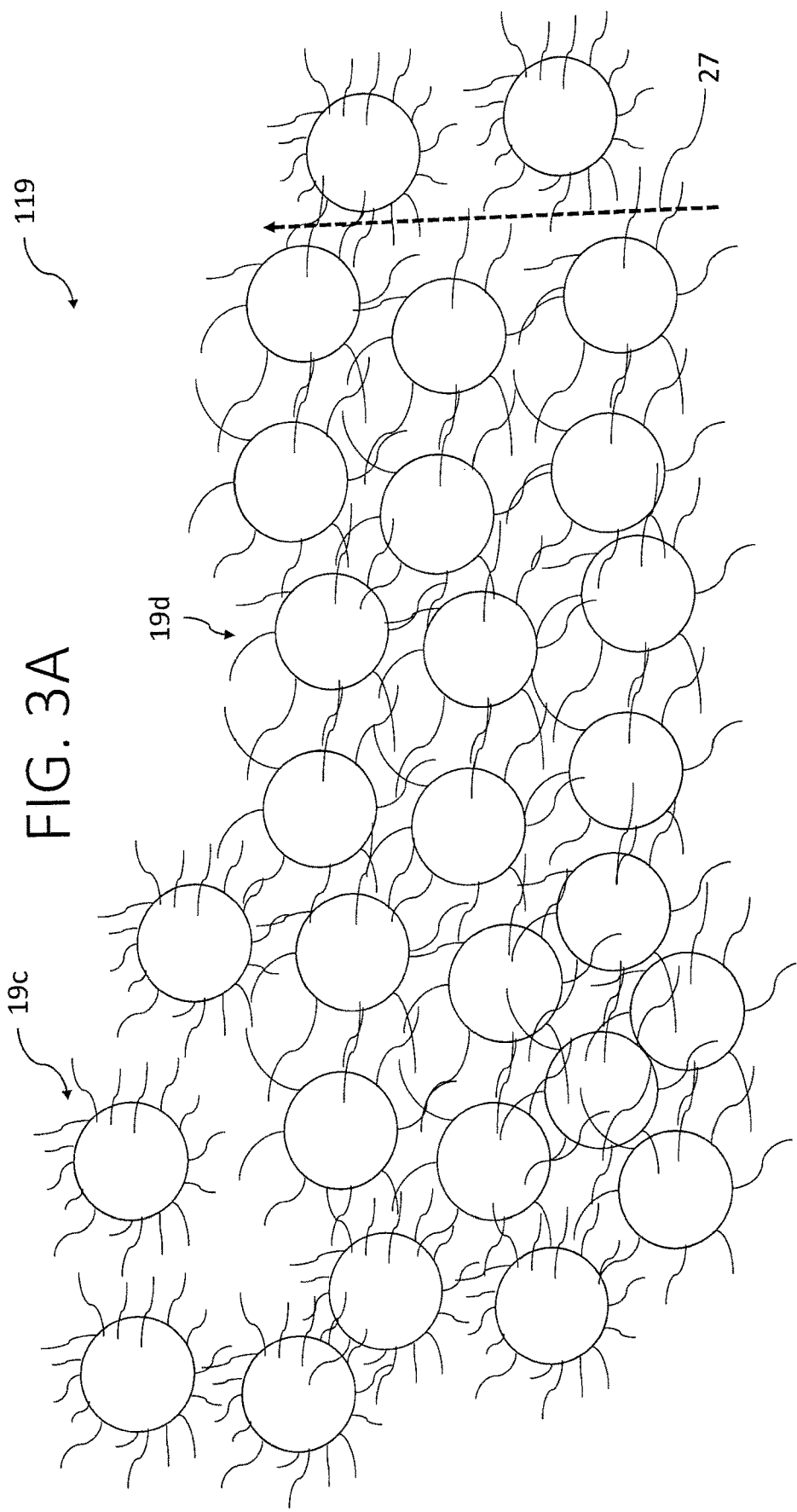

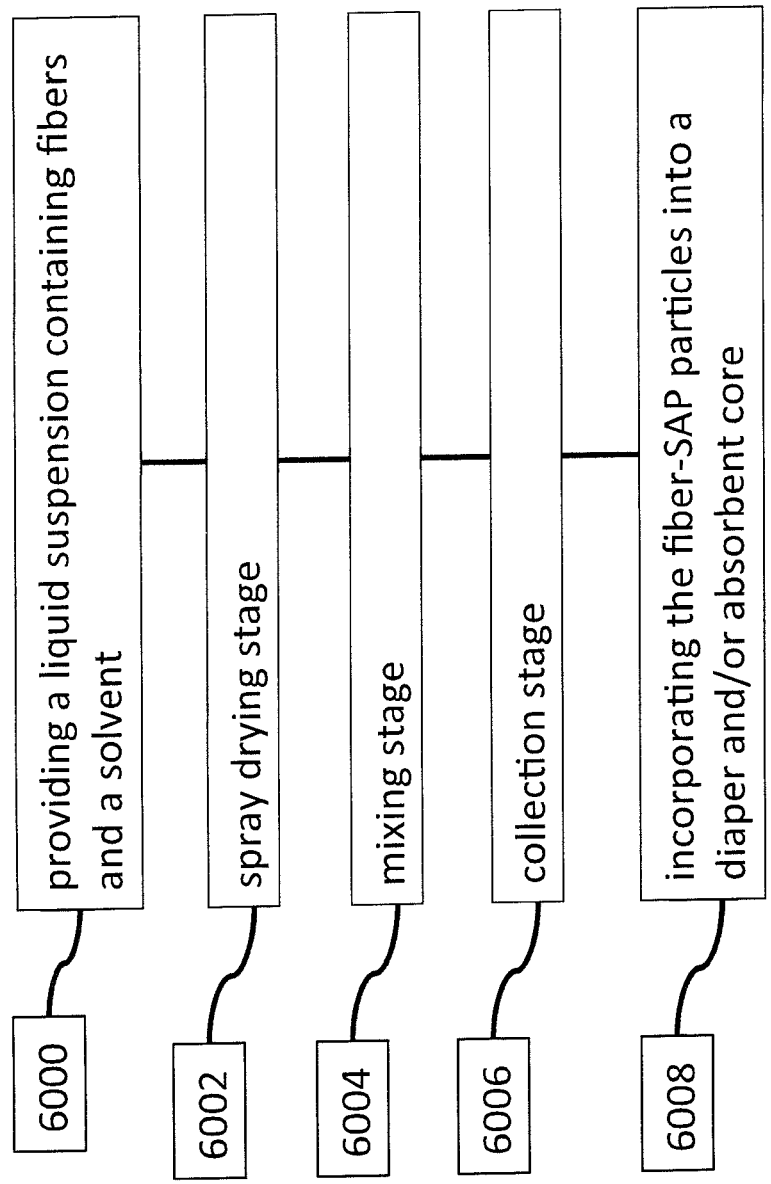

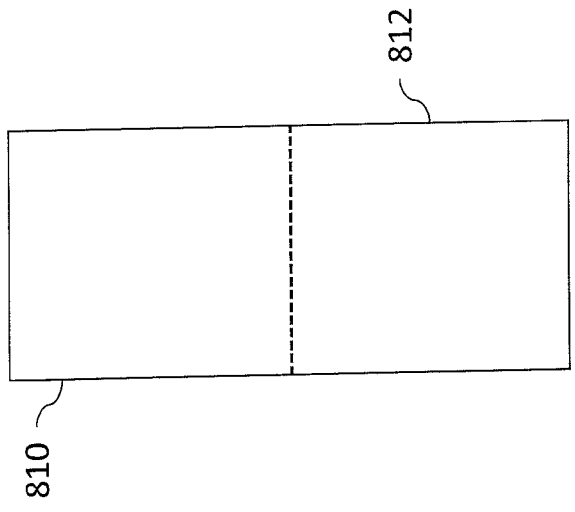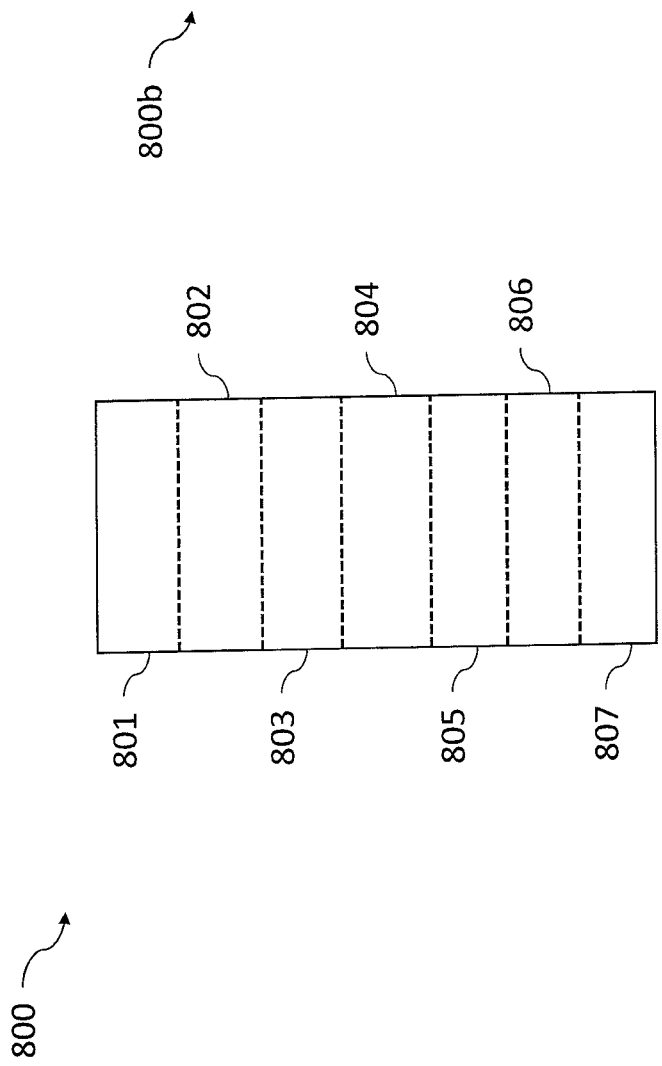
FIG. 8B
FIG. 8A

ABSORBENT MATERIAL, AND SYSTEM AND METHOD OF MAKING SAME

CROSS-REFERENCE TO RELATED APPLICATIONS

The present application is a Continuation application of U.S. application Ser. No. 15/905,813 filed on Feb. 26, 2018, which claims the benefit of U.S. Provisional Patent Application No. 62/463,714, filed on Feb. 26, 2017 ; and claims the benefit of U.S. Provisional Patent Application No. 62/482,277, filed on Apr. 6, 2017 . Each of these disclosures is hereby incorporated by reference for all purposes and made a part of the present disclosure.

FIELD

The present disclosure relates generally to an absorbent material, absorbent particles, a core composite, and a disposable absorbent article incorporating same. The disclosure also relates to systems and apparatus and methods suitable for making the same. At least some aspects of the disclosure are particularly suited for, or related to, disposable absorbent articles such as baby diapers, training pants for infants and young children and adult incontinence diapers and pants.

BACKGROUND

Absorbent articles, such as diapers, typically include three basic structural elements, including: (1) a topsheet that forms an inner surface; (2) a backsheet that forms an outer surface; and (3) an absorbent core that is interposed between the topsheet and the backsheet. The absorbent core is typically designed to contain and distribute fluid that passes through the topsheet. A typical absorbent core is made of a high or super absorbent polymer (SAP) stabilized by an absorbent matrix. SAP is commonly made out of materials such as polyvinyl alcohol, polyacrylates, various grafted starches, and cross-linked sodium polyacrylate. SAP can be in the form of particles, fibers, foams, web, spheres, agglomerates of regular or irregular shapes, and film. The absorbent matrix is typically a de-fiberized wood pulp or similar material. The absorbent matrix is very bulky relative to the topsheet, backsheet, and SAP.

It may be desirable to improve some aspects of absorbent cores, such as certain fluid handling capabilities including liquid absorption rates and other absorption properties, liquid distribution properties, and SAP immobilization within the absorbent core. It may also be desirable to provide systems and methods in which formation of the SAP and an associated fiber network is integrated into the systems and methods of making absorbent articles, cores, and materials.

U.S. Pat. No. 7,381,294 (Suzuki '294) and U.S. Pat. No. 6,794,557 (Klemp '557), provide background information on the design and manufacture of microfibrillated fibers relevant to the present disclosure, and disposable absorbent articles and products incorporating absorbent core compositions and structures. Accordingly, the disclosures of both Suzuki '294 and Klemp '557 are hereby incorporated by reference and made a part of the present disclosure, but only to the extent that incorporated subject matter provides background information and/or exemplary composites and processes suitable for use on, or with, the present compositions, articles, composites, systems, and methods. Thus, the incorporated subject matter shall not serve to limit the scope of the present disclosure.

SUMMARY

One aspect of the present disclosure relates to a method that includes partially drying a liquid suspension of fibers, and mixing the partially dried fibers with superabsorbent particles (SAP) such that at least some of the fibers attach to at least some of the SAP, forming fiber-SAP particles.

Another aspects of the present disclosure relates to an apparatus for forming a superabsorbent particles having fibers attached thereto. The apparatus includes a fiber drying chamber having an inlet for supplying a fiber-liquid suspension supply, and an atomizer at the inlet positioned to direct atomized fiber-liquid suspension into the drying chamber. Partially dried fibers and liquid are received in the chamber. The apparatus includes a mixing chamber in communication with the drying chamber to receive at least partially dried fibers from the drying chamber. The mixing chamber has an inlet for directing a supply of superabsorbent particles into said mixing chamber.

Another aspect of the present disclosure relates to a method of forming superabsorbent particles (SAP) with a plurality of fibers attached thereto and extending outward from an outside surface thereof. The method includes introducing a fiber-liquid suspension into a first zone by atomizing said liquid suspension and directing partly spray dried fibers and vapor from the suspension into said first zone. The method includes receiving the spray dried fibers in a second zone. The method includes introducing SAP into the second zone, including urging mixing therein of the SAP and partly dried fibers. Fibers are supported on the SAP and extend therefrom.

One aspect of the present disclosure relates to a method of forming fiber-SAP particles. The method includes introducing fibers into a chamber and introducing superabsorbent particles (SAP) into the chamber. The fibers and SAP mix such that at least some of the fibers attach to at least some of the SAP, forming fiber-SAP particles. In a further aspects, the fibers are introduced as or in a fiber-liquid suspension.

Other aspects of the present disclosure relate to a fiber-SAP particle that includes a superabsorbent core particle (SAP core particle) and a plurality of fibers attached to the SAP core particle.

Still further aspects of the present disclosure relate to an absorbent composite that includes a substrate, a cover layer, and a network of fiber-SAP particles positioned between the substrate and the cover layer. Each fiber-SAP particle includes a superabsorbent core particle (SAP core particle) and a plurality of fibers attached to the SAP core particle.

Another aspect of the present disclosure relates to an absorbent article that includes a chassis and an absorbent core composite supported on the chassis. The absorbent core composite includes a substrate, a cover layer, and a network of fiber-SAP particles positioned between the substrate and the cover layer. Each fiber-SAP particle includes a superabsorbent core particle (SAP core particle) and a plurality of fibers attached to the SAP core particle.

Another aspect of the present disclosure relates to a system for forming fiber-SAP particles. The system includes a chamber, a fiber-input component (e.g., a spray drying apparatus) positioned to introduce fibers into the chamber, and a SAP-input component (e.g., piping, supply, and/or nozzle) positioned to introduce SAP into the chamber. The chamber includes a fiber/SAP mixing zone and a fiber-SAP particle collection zone that is downstream of the fiber/SAP mixing zone.

Another aspect of the present disclosure relates to a method of making a pulpless absorbent material. The method includes providing microfibrillated cellulose fibers (MFC), and spray drying the MFC as a low consistency aqueous suspension into a fluidized bed containing superabsorbent (SAP) particles. The suspension includes a suspending liquid that is water or a mixture of water/alcohol. The method includes mixing the MFC fibers with the superabsorbent particles in the fluidized bed chamber. The mixing causes a multiplicity of fibers of the MFC to attach to each superabsorbent particle.

Another aspect of the present disclosure relates to a method of making a pulpless absorbent material. The method includes providing microfibrillated cellulose fibers (MFC), and mixing the fibers with superabsorbent (SAP) particles. The mixing may include mixing MFC with superabsorbent particles in a liquid suspension to cause a multiplicity of the fibers to attach to each superabsorbent particle. The attachment is due to residual water or alcohol in the chamber activating the SAP particle surface for fiber attachment. The method includes evaporating residual liquid in a drying process after the mixing step. Drying the mixture forms a finished mix of MFC and SAP, with a multiplicity of fibers attached to SAP particle. In some aspects, after the mixing step, the method includes directly feeding dry finished material mix of the MFC and SAP onto a substrate into a diaper machine to form an absorbent core.

Another aspect of the present disclosure relates to a method of making a pulpless absorbent material that includes providing microfibrillated or nanofibrillated cellulose fibers (FC), and mixing the FC with superabsorbent particles. In some aspects, the FC is provided by spray drying, thereby removing liquid content from the FC. The mixing of FC with SAP includes introducing FC into a fluidized bed containing superabsorbent (SAP) particles such that a multiplicity of fibers attach to each superabsorbent article. In some aspects, the MFC and superabsorbent particles are mixed in a liquid suspension. The attachment is due to residual water or alcohol in the chamber activating the SAP particle surface for fiber attachment. The method may include evaporating residual liquid in a drying process after the mixing to form a finished mix of MFC and SAP having a multiplicity of fibers attached to each SAP particle. The method may include, after mixing, directly feeding dry finished material mix of MFC and SAP onto a substrate into a diaper machine to form an absorbent core.

Another aspect of the present disclosure relates to a method of making a pulpless absorbent material that includes providing microfibrillated cellulose fibers, nanofibrillated cellulose fibers, or mixtures thereof (collectively "FC"), and mixing (e.g., in a mixing zone) the fibers with superabsorbent (SAP) particles, such that a multiplicity of fibers attach to each superabsorbent particle. The FC may be in a liquid suspension, which may be provided by atomization, such as via spray drying. The spray drying creates water-based droplets. In some aspects, the FC is spray dried into a heated environment. The spray drying results in solid fibers floating in the air. In some aspects, the fibers are dryer and less entangled after floating in the heated environment. In some aspects, the SAP is introduced after and/or downstream of the spray drying, such that the fibers attach to the surface of individual SAP particles. In some aspects, the method includes mixing additives with the FC and SAP, optionally within a mixing zone downstream of spray drying the FC. The method includes collecting a mixture of FC coated SAP after the mixing step, and optionally drying the mixture to remove residual liquid therefrom. In some aspects, the drying includes using infrared energy, hot air, or fluidized bed approach to remove residual liquid therefrom.

While the embodiments shown and described herein use a spray drying method, in some aspects the method may include use of ultrasonic drying, or may use a wet processing that uses a solvent slurry of fibers in conjunction with subsequent drying and solvent recovery steps. Ultrasonic drying imparts vibrations (e.g., at a resonant frequency) at ultrasonic frequencies to the liquid suspension, sheer thinning the liquid suspension, which allows the liquid suspension to flow more easily (e.g., through a nozzle). In some aspects, ultrasonic drying results in partial drying of the liquid suspension of fibers prior to atomization. Ultrasonic drying dewaters the liquid suspension and results in a greater degree consistency to the liquid suspension prior to introducing the liquid suspension into the chamber 24. One skilled in the art would understand that the liquid suspension is not limited to being introduced via spray drying or ultrasonic drying, but may be introduced via any of methods capable atomizing the liquid suspension to form an aerosol thereof.

Other aspects of the present disclosure relate to an absorbent material including superabsorbent particles, each particle having multiple fibers attached to an outside surface thereof. The fibers may be cellulose fibers, such as microfibrillated cellulose fibers, nanofibrillated cellulose fibers, or combinations thereof.

Some aspects of the present disclosure relate to a disposable absorbent article including a chassis and an absorbent core composite supported thereon. The absorbent core composite includes a network of superabsorbent particles (SAP) with cellulose fibers attached to an outside surface thereof. The fibers may be microfibrillated cellulose fibers, nanofibrillated cellulose fibers, or combinations thereof.

Another aspect of the present disclosure relates to a method for making absorbent particles. The method includes spray drying a liquid suspension (e.g., into a fluidized bed chamber) of fibers in solvent (e.g., water and/or ethanol), such that the fibers interact with SAP. The liquid suspension may be spray dried at an initial or top-located stage in the fluidized bed chamber. The spray drying may include use of an atomizer and nozzle (gun) to introduce the liquid suspension into a heated environment or zone in a heated spray stage of the method. The spray drying the liquid suspension increases the surface area of the liquid suspension, at least partially drying the fiber of the liquid suspension. The spray drying the liquid suspension also increases the amount of vaporous moisture present in the fluidized bed chamber; thereby: (1) wetting a surface of the SAP; (2) resulting in increased stickiness of the SAP surface; and (3) increasing a propensity of the SAP to attach with the fibers. A spray zone of the fluidized bed chamber may be located upstream of a mixing zone or stage of the fluidized bed chamber. At least some of the fibers adhere to the SAP, forming fiber-SAP particles. At least a portion of at least some of the adhered fibers of the fiber-SAP particles extend from the SAP, normal to a surface of the SAP. Some aspects include a mixing stage, where SAP, or SAP and additives, are introduced and mixed with the fibers. Some aspects include a collection stage in which the fiber-SAP particles are collected, optionally followed by a drying stage in which the collected fiber-SAP particles are dried. In certain aspects, the fiber-SAP particles are incorporated into a diaper, absorbent core, or combinations thereof. Turbulent mixing may occur in the mixing zone, such that at least partially dry fibers are mixed with the SAP. The flow path of introduction of the fibers is generally perpendicular to flow path of the introduction of the SAP. The mixing zone or stage includes a nozzle or inlet for additive particles or constituents. Some aspects of the method includes controlling flow or input of the spray dried fibers, the SAP, and any additives. The adherence between the fibers and the SAP occurs via adhesion, hydrogen bonding, or other interactions between the fibers and SAP.

In some aspects of the method, the fiber, SAP, fiber-SAP, or combinations thereof are functionalized. The fibers may be functionalized prior to introduction to the spray drying apparatus. The SAP may be functionalized prior to introduction to the fluidized bed chamber. The fibers may include MFC fibers, nano-fibrillated cellulose fibers, pulp fibers that are not micro- or nano-fibrillated, textile fibers, or combinations thereof.

In some aspects, SAP is mixed with additives prior to entry into the fluidized bed chamber, the liquid suspension is mixed with additives prior to entry into the fluidized bed chamber, or combinations thereof. Regardless of when and how they are introduced, the additives introduced into the fluidized bed chamber may include metal ions, polyelectrolyte complexes, nanocellulose, clay bentonite particles, cross linking particles, or combinations thereof.

The method may include a corona treatment stage, which may be downstream of the spray dry stage and upstream of the collection stage. The corona treatment stage may also be downstream of or at least partially coincident with mixing stage. The corona treatment initiates one or more chemical reactions (e.g., crosslinking) within the fluidized bed chamber. Certain aspects of the method include a crosslinking step to crosslink at least the surface of the SAP.

In certain aspects of the method, the heating zone within the fluidized bed chamber is heated to a temperature above the ambient temperature surrounding fluidized bed chamber (e.g., above room temperatures).

The method may include wetting a surface of the SAP. The surface of the SAP may be wetted using vapour formed from spray drying the liquid suspension, additional vapour introduced into the fluidized bed chamber, or combinations thereof.

The method may include forming channels from a surface of SAP to an interior of SAP with the fibers. For example, during mixing, adhesion, and/or bonding, at least some of the fibers may become at least partially embedded into the surface of SAP particles, such that the embedded fibers extend into the interior of the SAP particles, below the surface of the SAP particles. The embedded fibers may function as channels for introduction of fluids into the interior of the SAP particles.

In some aspects, wicking channels or paths are formed between adjacent fiber-SAP particles.

In some aspects, the fiber-SAP particles are incorporated into a diaper, absorbent core, or combinations thereof.

Another aspect of the present disclosure relates to a fiber-SAP particle that includes SAP particles and a plurality of fibers adhered to the SAP particles. At least a portion of at least some of the fibers extend from the SAP particles, normal to an outer surface of the SAP particles. At least some of the fibers may be at least partially embedded into the SAP, providing a path or channel into an interior of the SAP; thereby, increasing absorption rate for the SAP. The liquid may absorb into the embedded fiber and flow within the fiber into an interior of the SAP. In some aspects, the surface of the fiber-SAP particles is at least partially crosslinked. The fibers attached to the SAP may have a length that is shorter than, equal to, or longer than the average diameter of the SAP particles.

Another aspect of the present disclosure relates to an absorbent article including a plurality of fiber-SAP particles incorporated therein. The fibers attached to SAP may act as shock absorbers; thereby, resulting in less compression of the SAP during use and maintaining swellablity of the SAP. Adjacent fiber-SAP particles in the article may remain at least partially spaced apart, forming wicking paths between the adjacent fiber-SAP particles. The wicking paths allow for fluid flow there-between.

Another aspect of the present disclosure relates to a fiber-SAP particle including a particle core of SAP and a plurality of fibers extending from the SAP. Each fiber has a first end that is bonded, attached, adhered, or otherwise in engaged with the SAP, and a free end that is not bonded, attached, adhered, or otherwise engaged with the SAP.

Certain aspects of the present disclosure provide for methods and systems for forming a structural unit that includes or consists of SAP and MFC (or another fiber). In such a structural unit of SAP and MFC (i.e., a fiber-SAP particle), the SAP and MFC are intimately connected (i.e., is a single component as opposed to two components imply mixed together) and function synergistically together during use for providing absorbency and other absorbent article functions.

Certain aspects of the present disclosure provide for methods and systems for producing the fiber-SAP particles that use low-levels of solvent/liquid during the formation thereof. Methods and systems that use low-levels of solvent/liquid provide an elimination of, or at least a reduction in, the use of drying, solvent recovery processes, and other such process steps associated with wet processes/systems, due to the low solvent content of the constituents introduced into the reaction zone (e.g., the fluidized bed chamber).

BRIEF DESCRIPTION OF THE DRAWINGS

So that the manner in which the features and advantages of embodiments of the present disclosure may be understood in more detail, a more particular description of the briefly summarized embodiments above may be had by reference to the embodiments which are illustrated in the appended drawings that form a part of this specification. It is to be noted, however, that the drawings illustrate only various exemplary embodiments, and are therefore not to be considered limiting of the scope of this disclosure, as it may include other effective embodiments as well.

FIG. 3A is a simplified illustration of a network of fiber-SAP particles in accordance with certain aspects of the present disclosure;

FIG. 6 is a flow chart of a method of making fiber-SAP particles in accordance with certain aspects of the present disclosure;

FIGS. 8A and 8B are simplified illustrations of systems including multiple zones in accordance with certain aspects of the present disclosure;

DETAILED DESCRIPTION

Figure 1:
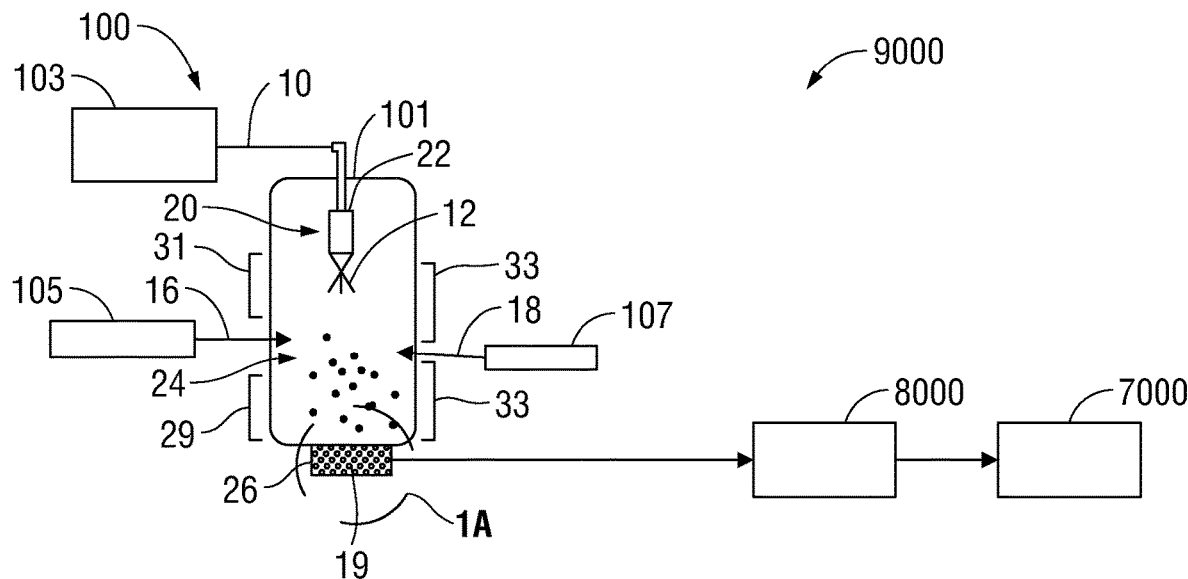
FIG. 1 is a simplified illustration of an apparatus and method of making an absorbent material, according to the present disclosure.
Figure 1A:
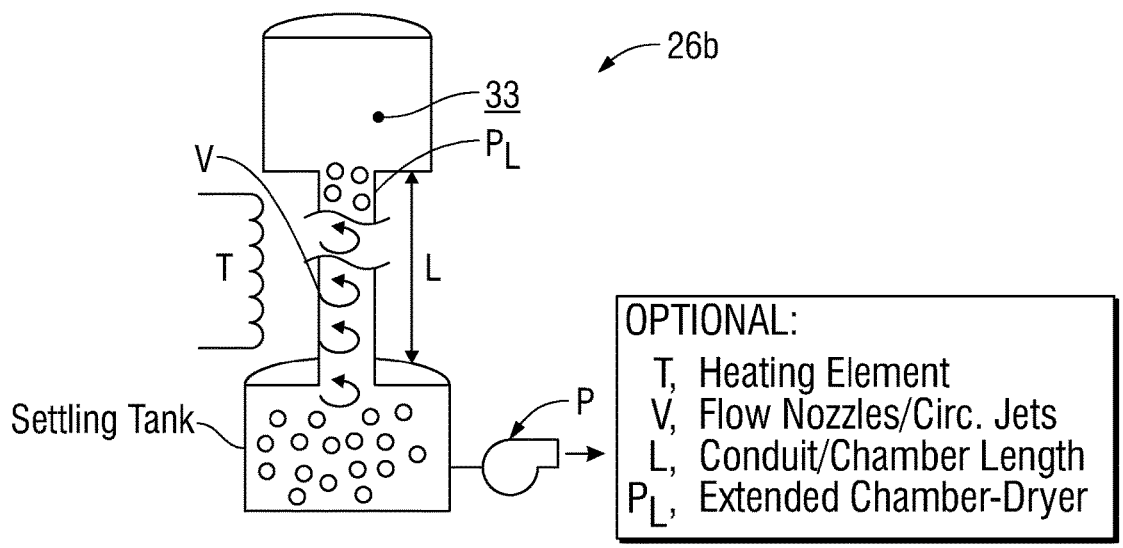
FIG. 1A is a simplified illustration of a collection zone or apparatus, according to the present disclosure.

Embodiments of the present disclosure will now be described more fully with reference to the accompanying drawings, which illustrate various exemplary embodiments. The disclosed concepts may, however, be embodied in many different forms and should not be construed as being limited by the illustrated embodiments set forth herein. Rather, these embodiments are provided so that this disclosure will be thorough as well as complete and will fully convey the scope to those skilled in the art and the best modes of practicing the embodiments. For example, many of the exemplary descriptions provided herein are concerned with absorbent material for incorporation into diapers and training pants for infants and young children. Aspects of the disclosure described may, however, be equally applicable to designs for and the manufacture of other products. One set of applications is directed, however, to the manufacture of an absorbent material well suited for direct incorporation as the core composition for an absorbent article, such as a diaper or training pants. The methods and products can be incorporated directly, and linearly, into or as the core forming stage of a mostly linear system and method of manufacturing such absorbent articles.

Disposable absorbent articles contemplated in this disclosure include, but are not limited to, training pants, pull-on diapers, disposable underwear, and adult incontinence garments. As for training pants, these garments may be used by young children to facilitate a child's transition from using diapers to wearing regular underpants (i.e., during toilet training). Training pants and other disposable pull-on pants may have closed sides such that the user or caregiver raises the garment about the user's legs to wear the garment and slips the garment downward about the user's legs to take it off. These articles and garments are collectively referred to herein as "absorbent pants" or "pants products."

Microfibrillated cellulose, and its methods of manufacture, as taught and described by Suzuki '294 provides a suitable source of originating material or feedstock for certain aspects of the present method. It should be noted that while the Suzuki '294 prior patent publication provides some discussion on making MFC and then incorporating the same into absorbent articles, the present disclosure is, in at least one respect, more particularly directed to providing an improved system and method of making an absorbent article, core composition, and/or absorbent materials. More specifically, one directive of the present disclosure is to provide a method and system, whereby and wherein the fibrous or cellulose product\fiber network and its formation are seamlessly integrated into the method of making the article and into the absorbent material itself. On the other hand, the Klemp '557 disclosure may provide exemplary product applications and core designs, for which the product of certain aspects of the present disclosure may be suitable.

In accordance with one aspect of the present disclosure, a microfibrillated cellulose, produced as taught by Suzuki '294, is spray dried as a low consistency aqueous suspension into a fluidized bed containing superabsorbent particles (SAP). The suspending liquid may be water or a mixture of water/alcohol, for example. Mixing of the microfibrillated cellulose fibers with the superabsorbent particles in a fluidized bed chamber, according this aspect, causes a multiplicity of fibers to attach to each superabsorbent particle. The attachment mechanism may arise from some residual water or alcohol in the chamber activating the SAP particle surface for fiber attachment. This residual liquid is evaporated in a subsequent drying process. The dry finished material may then be directly fed into a diaper machine to form the absorbent core for a finished diaper.

The fibers according the present method and product may be micro-fibers, nanofibers, or combinations thereof. As used herein, "micro" in reference to fibers refers to fibers having an average diameter ranging from 100 to 1000 nanometers, or from 200 to 900 nm, or from 300 to 800 nm, or from 400 to 700 nm, or from 500 to 600 nm; and an average length of at least one micron and up to several microns. As used herein, "nano" in reference to fibers refers to fibers having average diameters that are typically in the range of about 10 to about 100 nm, or from about 20 to about 90 nm, or from about 30 to 80 nm, or from 40 to 70 nm, or from 50 to 60 nm; and an average length of from 50 to 3,000 nm, or from 100 to 2500 nm, or from 200 to 2000 nm, or from 300 to 1500 nm, or from 400 to 1000 nm, or from 500 to 900 nm, or from 600 to 800 nm. As one skilled in the art would understand, fiber dimensions are typically measured using optical or electron microscopy.

The resulting fiber coated SAP (fiber-SAP) is particularly suited to the production of pulpless absorbents for use in diapers and other hygiene products. The microfiber cellulose is hydrophilic and the fiber assembly at the surface of the SAP allows faster liquid absorption into the particle in comparison to an otherwise identical SAP that is not coated or attached to fibers (i.e., is not a fiber-SAP), better distribution of liquid from particle to particle in comparison to an otherwise identical SAP that is not coated or attached to fibers (i.e., is not a fiber-SAP), better absorption by the SAP under load in comparison to an otherwise identical SAP that is not coated or attached to fibers (i.e., is not a fiber-SAP), and better immobilization of the SAP caused by higher particle-particle interaction in comparison to an otherwise identical SAP that is not coated or attached to fibers (i.e., is not a fiber-SAP). In some aspects, the absorbent material disclosed herein does not include any absorbent matrix other than the fibers attached to the SAP core particle.

System/Apparatus for Producing Fiber-SAP Particles

An exemplary system suitable for use in producing the fiber-SAP particles disclosed herein will now be briefly described. Certain aspects of the present disclosure relate to systems and apparatus for forming fiber-SAP particles. With reference to FIG. 1, fiber-SAP forming system 9000 includes fiber-SAP forming apparatus 100, including fluidized bed chamber 101. The internal cavity of fluidized bed chamber 101 defines chamber 24. Apparatus 100 includes a fiber-input device, here shown as spray drying device 20, which includes atomizer and nozzle (gun) 22. A fiber supply, here shown as MFC supply 103 provides liquid suspension 10 of fibers to atomizer and nozzle (gun) 22. Coincident with and/or downstream of spray drying device 20, fluidized bed chamber 101 includes spray zone 31, which may be a heated spay zone. Coincident with and/or downstream of spray zone 31, fluidized bed chamber 101 includes mixing zone 33. Coincident with and/or downstream of mixing zone 33, fluidized bed chamber 101 includes corona treatment zone 29. Downstream of mixing one 33, fluidized bed chamber 101 includes collection zone 26. Apparatus 100 includes SAP supply 105 and optionally additives supply 107, which may both be coincident with mixing zone 33, for supplying SAP 16 and additives 18, respectively. Downstream of collection zone 26, system 9000 includes system or apparatus for forming an absorbent core 8000 using the fiber-SAP particles 19. Downstream of system or apparatus for forming an absorbent core 8000, system 9000 includes system or apparatus for forming an absorbent articles 7000 using the absorbent cores formed in system 8000. In the interest of clarity, systems 8000 and 7000 are not detailed herein. However, one skilled in the art would understand that systems 8000 and 7000 may be any system suitable for formation of absorbent cores and absorbent articles, and in fact, may be a single system, rather than two separate systems, as shown. For example, Suzuki '294 discloses suitable systems and methods for producing absorbent cores and articles using SAP particles, which may be suitable for use with the presently disclosed fiber-SAP particles 19. In some aspects, the dried, finished absorbent material (i.e., dried fiber-SAP particles 19 or a network thereof) are fed directly into a diaper machine to form the absorbent core for a finished diaper, without any intermediate processing therebetween.

Having now described an exemplary system for forming fiber-SAP particles, a method of forming fiber-SAP particles will now be described with reference to the system of FIG. 1.

Spray-Drying

With reference to FIG. 1, the introduction of fibers (e.g., cellulose fibers) into chamber 24 is performed in a manner such that fibers are dispersed and/or spread within chamber 24. For example, the fibers may be introduced such that an aerosol is formed (i.e., a colloid of the fibers and optionally liquid droplets in air or another gas), with the fibers suspended within the air or other gas within chamber 24. One example of such a method of introducing the fibers is spray drying. This entails fibers being presented in liquid suspension 10, which is then atomized such that liquid-based droplets 12 are created and dispersed within chamber 24. Atomization of liquid suspension 10 allows for all or substantially all of the liquid of liquid suspension to readily flash off of fibers into the surrounding environment within the chamber 24. Such flashing off of the liquid is a convenient way of reducing the volume or amount of liquid in the finished or near-finished absorbent product, which may be dried or removed in a subsequent stage.

Introduction of liquid suspension 10 of fibers occurs via a spray at an initial or top-located stage within an upper zone of chamber 24. In some aspects, liquid suspension 10 is a slurry of fiber and solvent (MFC slurry). The solvent may be water, a low molecular weight alcohol (e.g., ethanol and/or isopropanol), another solvent, or combinations thereof. Ethanol and other low molecular weight alcohols may not induce as high a degree of swelling of the SAP as does water, evaporates at a lower temperature than water, dries more quickly from the fibers than water, and has a lower viscosity than water. An atomizer and nozzle (gun) 22 may introduce liquid suspension 10 into a heated environment or zone of the apparatus 100, such as into heated spray zone or stage 31. Heated zone may be heated to sufficient to promote evaporation of the liquid from the fibers. For example, if the liquid is water, the heated zone may be at a temperature of at least 100° C., or from 180° C. to 200° C. In some aspects, heated air is recirculated within the mixing chamber 33 for vaporization of the liquid from the fibers. Spray drying the liquid suspension 10 increases the surface area of the liquid suspension 10, at least partially drying the fiber of liquid suspension 10 within chamber 24. Also, spray drying the fiber may increase the amount of vaporous moisture present in chamber 24 relative to the amount of vaporous moisture present in chamber 24 prior to spray drying liquid suspension 10 as a result of the introduction of the liquid as additional vaporous moisture. Increased vaporous moisture in chamber 24 may result in wetting of a surface of SAP 16 present in chamber 24 (i.e., deposition of moisture, such as water, onto the outer surface of SAP 16). Such wetting of the outer surfaces of SAP 16 may result in increased stickiness (e.g., increasing H-bonding) of the SAP outer surface, relative to the stickiness of the SAP outer surface prior to wetting, which increases the propensity of the SAP 16 to attach (e.g., H-bond) with the fibers of liquid suspension 10.

In some aspects, the liquid suspension of fibers includes from greater than 0 weight percent to 30 weight percent of fibers, or from 5 weight percent to 20 weight percent of fibers, or from than 10 weight percent to 15 weight percent of fibers, based on a total weight of the liquid suspension. In certain aspects, the liquid suspension of fibers includes up to 20 weight percent of fibers, or from 0.1 to 10 weight percent of fibers, or from 1 to 8 weight percent of fibers, or from 2 to 7 weight percent of fibers, or from 3 to 5 weight percent of fibers based on a total weight of the liquid suspension.

Regardless of the particular form of introduction used to atomize the liquid suspension, the fibers and liquid are a single-component when formed into an aerosol, rather than being separate components.

In some aspects, coincident with or downstream of the spray drying zone (or other introduction method) an initial stage of pre-drying of the fibers of the liquid suspension occurs to reduce the liquid content of the fibers. In this pre-drying zone, the liquid suspension of fibers is atomized and in dynamic motion within the chamber 24, so as to promote and maintain the separation of individual fibers of the liquid suspension of fibers and prevent aggregating or agglomerating thereof. Such dynamic motion also promotes the drying (e.g., evaporation) of the liquid from the fibers and into the surrounding environment (e.g., into the air within the chamber 24).

Mixing Zone

The spray zone of apparatus 100 may be located above and\or upstream of mixing zone or stage 33 of apparatus 100. In mixing zone 33, turbulent mixing may be facilitated and/or encouraged, and the nearly dry (drier and/or less entangled) fibers are mixed with a supply of superabsorbent particles 16. In some aspects, the turbulent mixing may be facilitated and/or encouraged by introducing SAP 16 into chamber 24 in a direction that is at an angle greater than 0 degrees relative to the direction in which liquid suspension

10 is introduced into chamber 24, such as an angle ranging from 15 degrees to 180 degrees, or rom 20 degrees to 150 degrees, or from 40 degrees to 120 degrees, or from 60 degrees to 100 degrees, or from 70 degrees to 90 degrees. Additionally, the use of spray nozzles for the introduction one or more of liquid suspension 10, SAP 16, and additives 18, the use of heat, or combinations thereof may facilitate such turbulent mixing. SAP 16 may be introduced through a sidewall of chamber 24 and generally perpendicular to the supply of fibers (i.e., liquid suspension 10), such as through an inlet, piping, and/or nozzle(s) engaged with and/or through the sidewall of chamber 24. In some aspects, apparatus 100 at mixing zone or stage 33 may be equipped with further inlet, piping, and/or nozzle for the introduction of additive particles 18 or constituents into chamber 24. Within mixing zone 33, the fibers are deposited onto or otherwise attached to SAP 16 particles. For example, SAP 16 may be introduced into an aerosol of the fibers, such that the SAP intermixes with the fibers within the colloid of fibers.

Apparatus 100 may allow for ready control of flow or input of the spray dried fibers, the SAP 16, and additives 18, such as via the use of valves and nozzles, and manual and/or automatic controllers for such valves and nozzles; thereby, making possible an array of final product chemistries and resulting mechanical and physical properties of fiber-SAP particles. In some aspects, air flow is directed to maintain the fibers, SAP and any other components within chamber 24 suspended within the air, mixing within the chamber 24. The air flow may be controlled and/or directed to allow the fiber-SAP particles 19 to settle and collect when dry and mixed together. The constant agitation of the SAP and fibers caused by the turbulent mixing minimizes agglomeration of during the drying process. In some aspects, the air flow provided and/or controlled via one or more fans positioned to provide air flow into the chamber 24. The fans may be configured and/or arranged to provide an eddy current within the chamber 24.

As such, in some aspects the fibers are pre-dried, the SAP is wetted and thus activated, and the pre-dried fibers and wetted SAP are mixed together for attachment therebetween in a single reaction chamber.

Collection Zone

Below and\or downstream of mixing zone 33, the volume, network, or collection of fiber coated SAP (fiber-SAP) 19 is concentrated and\or collected at collection zone or stage 26 of apparatus 100. Collection zone 26 is located at the bottom of chamber 24; however, one skilled in the art would understand that apparatus 100 is not limited to this configuration. Fiber-coated SAP 19 settle within collection zone 26, which may be isolated from the turbulence of mixing zone 33. Within collection zone 26, fiber-SAP particles 19 form a higher density conglomerate or collection of fibers, SAP, fiber-SAP 19, or combinations thereof, relative to the density of such constituents within mixing zone 33. Within collection zone 26, individual fiber-SAP particles 19 are positioned adjacent other individual fiber-SAP particles 19, such that adjacent individual fiber-SAP particles 19 interact, touch, or otherwise engage one another. Such interaction between adjacent fiber-SAP particles 19 may involve interactions between the fibers of fiber-SAP particles 19, interactions between the fibers of one fiber-SAP particle 19 and the SAP of the adjacent fiber-SAP particle 19, interactions between the SAP of the fiber-SAP particles 19, or combinations thereof. Once settled within collection zone 26, a network of fiber-SAP particles 19 is formed. The network of fiber-SAP particles 19 may optionally be subjected to drying to remove any residual liquid therefrom. Such drying may be facilitated by heat, air flow, residence time within collection zone 26, or combinations thereof.

In some aspects, the process is a batch process in which fiber-SAP particles 19 collect within collection zone and are retrieved therefrom batch-wise (e.g., manually).

In other embodiments, the process is a continuous process or a semi-continuous process. With reference to FIG. 1A, a collection zone 26*b* of a continuous process is shown. Collection zone 26*b* may include a conduit or chamber having associated therewith a length L, flow path V, and temperature T sufficient to provide fiber-SAP particles 19 with a residence time therein to be dry upon entering settling tank below the conduit or chamber. The flow path V may be at least partially controlled via flow nozzles and/or circulating jets in fluid communication with the conduit or chamber. The temperature T may be controlled via heating element(s), for example. Thus, the collection zone 26*b* may be an extended chamber dryer, ensuring that the fiber-SAP particles 19 are dry when pumped therefrom via pump P. One skilled in the art would understand that other system and apparatus configurations and arrangements may be used to achieve selective separation of fiber-SAP particles from pre-wet, partially swollen SAP particles in a continuous process. Such separation methods may rely on differences between densities, drag, weights, particle size, other properties, or combinations thereof for the selective output or retrieval of fiber-SAP particles rather than pre-wet, partially swollen SAP particles. Such separation methods may utilize eddy currents or circumferential currents that direct the selected particles to an outlet. Such currents may be provided by jets that directed air flow.

Corona Treatment Zone

In some aspects, apparatus 100 includes a corona treatment zone or stage 29, which may be downstream of the spray dry apparatus 20 and upstream of collection zone 26. Corona treatment zone or stage 29 may be downstream of or at least partially coincident with mixing zone or stage 33. Corona treatment of fibers, SAP 16, and/or fiber-SAP particles 19 may initiate one or more chemical reactions within the chamber 24. One skilled in the art would understand that apparatus 100 may include, in addition to or instead of corona treatment zone or stage 29, other chemical, thermal, and/or physical treatment zones or stages. Corona treatment may promote bonding between the fibers and SAP 16.

In some aspects, corona charges the surface of the SAP to make the SAP more hydrophilic (i.e., activates the surface of the SAP for wetting (makes the SAP wettable)), promotes ionization of constituents within the chamber, initiates crosslinking of molecules of the SAP with other molecules of the SAP, initiates crosslinking of molecules of the fiber with other molecules of the fiber, initiates crosslinking of molecules of the SAP with molecules of the fiber, or initiates other chemical reactions between constituents within the chamber 24.

Crosslinking

In some aspects, the outer surface of the SAP 16 and/or fiber-SAP particles 19 may be at least partially crosslinked, which may reduce the occurrence of gel blocking when fiber-SAP particles 19 absorb liquids. In some aspects, crosslinking on the surface of the fiber-SAP particles 19 may be initiated by the corona treatment. In certain aspects, the outer surface of the SAP 16 introduced into the chamber 24 may be at least partially crosslinked prior to introduction into chamber 24, and the corona treatment may be used to further (e.g., fully) crosslink the outer surface of the SAP 16. In other aspects, the outer surface of the SAP 16 introduced into the chamber 24 is not crosslinked prior to introduction into chamber 24, and the corona treatment is used to crosslink the previously un-crosslinked outer surface of the SAP 16. In still other aspects, the outer surface of the SAP 16 introduced into the chamber 24 may be fully crosslinked prior to introduction into chamber 24, and corona treatment is not used to further crosslink the outer surface of the SAP 16.

In some aspects, the SAP introduced into the chamber 24 is not crosslinked, or is partially crosslinked when introduced into the chamber 24. In some such aspects, the SAP is subsequently crosslinked within the chamber 24, such as via the introduction of crosslinking particles, Corona treatment, or combinations thereof. In some aspects, the SAP is not fully crosslinked when introduced into the chamber 24. In certain aspects, the SAP does not have a core-shell morphology, such that the SAP does not include an outer shell or surface that is more crosslinked than an inner core that is less crosslinked.

In some aspects, the fiber-SAP particles 19 include: (1) crosslinking between polymer chains of SAP core particle and other polymer chains of the SAP core particle; (2) crosslinking between polymer chains of the SAP core particle and polymer chains of the fibers; (3) crosslinking between polymer chains of the fibers and other polymer chains of the fibers; or (4) combinations thereof.

Fiber-SAP Bonding

Bonding between the fibers and SAP 16 to form fiber-SAP particles 19 may occur within mixing zone 33, downstream of mixing zone 33 but upstream of collection zone 26, within collection zone 26, downstream of collection zone 26, or combinations thereof. For example, in some aspects, fibers are coated onto but not yet bonded to SAP 16 when mixed in mixing zone 33 and/or when collected within collection zone 26. The bonding between the fibers and SAP 16 may be facilitated by drying, such that, as the network of fibers and SAP 16 within collection zone 26 dries, fiber-SAP particles 19 are formed. The bonding between the fibers and SAP 16 may occur via adhesion of fibers onto the surface and/or an interior portion of the SAP 16; via hydrogen bonding of the fibers with the surface and/or an interior portion of the SAP 16; via polymer chain entanglement of polymer chains of the fibers and polymer chains of the SAP 16; or via other forms of bonding, entanglement, adhesion, partial dissolution, attachment, engagement, or other interactions between the fiber and SAP 16.

In some aspects, the turbulence within the mixing zone 33 promotes substantial relative motion of the SAP 16 and any fibers attached to the SAP 16. Such turbulence causes the unattached portions (free ends) of the attached fibers to raise off the surface of the SAP 16. Additionally, such turbulence promotes drying of the SAP 16 and any fibers attached thereto, further strengthening the attachment between the fibers and SAP 16. Fibers that are attached to SAP 16, regardless of whether the fiber is embedded into the SAP 16, provide channels for fluid flow to the SAP 16, as the high surface area of the fibers provides additional surface area for absorption if insult (relative to the surface area of the SAP alone).

Functionalization

In some aspects, the fiber, SAP 16, fiber-SAP 19, or combinations thereof are functionalized. For example, the fiber may be functionalized (e.g., grafted) prior to introduction to the spray drying apparatus or after introduction into chamber 24. In some aspects, the SAP 16 may be functionalized (e.g., grafted) prior to or after introduction into chamber 24. In some aspects, additives 18 chemically react with fiber and/or SAP 16 to functionalize the fiber and/or SAP 16.

In some aspects, functionalization (the functional groups) applied (e.g., bonded to) to the fibers, such as ion exchange or odor-reducing functional groups or particles, acts on the insult (e.g., liquid insult) prior to the insult being absorbed and captured by the SAP core particle. Thus, if the fibers are functionalized with ion exchange properties, the insult may flow into the core SAP particle at a lower ionic strength, which provides the SAP with higher absorption capacities of the insult. If the fibers are functionalized with odor-reducing functional groups or particles, the insult may flow into the core SAP particle with a lower potential for creating malodors.

Additives

Additives 18 may be introduced to mix and/or react with fiber and/or SAP 16 to confer properties to the fiber-SAP particles 19 that are useful for hygiene products. Additives 18 may be mixed and/or reacted with fibers prior to or after introduction of fibers into chamber 24; mixed and/or reacted with SAP 16 prior to or after introduction of SAP 16 into chamber 24; mixed and/or reacted with fiber-SAP particles 19 within or downstream of apparatus 100; or combinations thereof. For example, and without limitation, additives 18 may include metal ions for antibacterial and odor reducing properties; polyelectrolyte complexes that may add cation exchange capabilities, which may increase the absorption capacity of SAP by removing multivalent ions from urine; clay bentonite particles; cross linking particles; other functional additives, such as if nanocellulose is used, that can provide biosensing functionality; or combinations thereof. In some aspects, the additives include carbon (e.g., activated carbon), ion exchange resins, or agar-agar. Additives 18 may include one or more adhesion promotors to promote adhesion between the fibers and SAP.

In some aspects, the fibers are treated (e.g., pre-treated prior to spray drying) with one or more additives. For example, the fibers may be pre-treated by combining the fibers with additives including, but not limited to: odor controlling additives, such as metal ions, such as Copper ($Cu^{+2}$), Silver ($Ag^{+1}$), Gold ion ($Au^{+1}$ and $Au^{+3}$), Iron II ion ($Fe^{+2}$), Iron (III) ion ($Fe^{+3}$), permanganate ion ($MnO_4^{-1}$), or combinations thereof; anti-bacterial additives, such as Silver ions and Copper (e.g., Cuprous oxide based additives); additives having ion-exchange capacity; or combinations thereof. Multivalent ions reduce ionic strength of urine and increase SAP absorbent capacity (e.g., grafted Polyacrylic (PAA) or polyitaconic (PIA) acid).

Fibers

In some aspects, the fibers of liquid suspension 10 include MFC fibers, nano-fibrillated cellulose fibers, pulp fibers that are not micro- or nano-fibrillated, textile fibers, or combinations thereof. In some aspects, nanofibrillated cellulose or a mixture of microfibrillated and nanofibrillated cellulose may be used. Nanofibers of the nanofibrillated cellulose may have a higher surface area in comparison to fibers of microfibrillated cellulose.

While the fibers are described herein as cellulose fibers, one skilled in the art would understand that the fibers may be other non-cellulose fibers, such as other hydrophilic fibers. Also, the fibers may be a mixture of different types and/or different sizes of fibers (e.g., a mixture of different hydrophilic fibers and/or a mixture of micro and nano fibers). In some aspects, in addition to or instead of cellulose, the fibers may include starch-based polymer fibers (e.g., polysaccharide fibers), polyethylene terephthalate (PET) fibres, polyethylene (PE) fibres, polypropylene (PP) fibres, alternative cellulose fibers (e.g., cotton fibers, bamboo fibers, flax fibers).

In some aspects, the use of nano-sized fibers, such as nano-fibrillated cellulose fibers, provides more fiber surface area per weight of fiber attached to the outer surface of the SAP. Fluid flow properties provided by the fibers are a surface phenomenon, such that insult flows along the surface of the fibers for introduction to the SAP core particle. Thus, providing more fiber surface area per weight of fiber attached to the outer surface of the SAP provides for increased fluid flow of insult to the SAP core particle.

Certain Advantages of the Method

Some aspects of the methods according to the present disclosure provide one or more of the additional, advantageous results of: (1) requiring less energy in drying or reducing water liquid content, at least in part, as a result of the use of atomization and optionally heating the chamber 24; (2) effecting a more uniform mixing and distribution of SAP or fibers, at least in part, as a result of the use of spray-drying to mix the fibers and SAP; (3) providing a more ready means of regulating or designing absorbent material properties or chemical, mechanical, and physical characteristics; and (4) allowing for more ready manipulation of the mixture constituents (e.g., SAP, fibers, additives), including the sequential or simultaneous addition of constituents, fiber-sap ratios, and\or the selection of additives. For example, the properties and characteristics of the absorbent material may be affected by one or more of: (1) the selection of the fiber sizes, including fiber lengths and widths (e.g., use of micro and/or nano fibers); (2) fiber properties, including denier; (3) the selection of the fiber-to-SAP ratio; (4) the optional functionalization of the fibers and/or SAP, such as by chemically bonding one or more functional groups with the fibers and/or SAP; and (5) the selection of additives to be incorporated with the fibers and SAP. One skilled in the art would understand that these and other parameters may be varied to modify the chemical, physical, and/or mechanical properties of the resulting fiber-SAP particles produced.

The resulting fiber-SAP composition provides a fiber network with one or more of: (1) increased surface (absorbent) area or fiber exposure, thereby enhancing fluid absorption properties; (2) increased fluid distribution between SAP and fibers; (3) faster absorbent rates; and (4) more physical\mechanical interaction between fiber coated SAP particles, thereby enhancing fluid distribution and absorption properties and\or reducing SAP migration (i.e., inhibiting migration of SAP during manufacture of absorbent articles and directing post-manufacturing).

Fiber-SAP Particles

Figure 2:
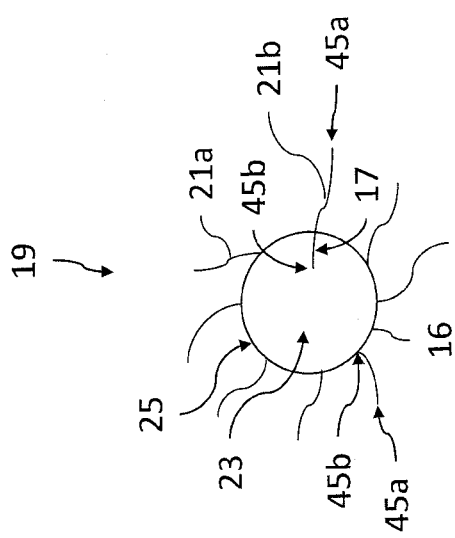
FIG. 2 is a simplified illustration of a fiber-SAP particle in accordance with certain aspects of the present disclosure.

With references to FIGS. 1 and 2, in some aspects fiber-SAP particle 19 includes a plurality of fibers 21a bonded (e.g., hydrogen bonded, ionically bonded, covalently bonded) with, attached to, adhered to, entangled with, coated onto, or otherwise engaged with SAP 16. At least some of the plurality of fibers 21a include a restrained end 45b (i.e., the end of the fiber 21a that is, in some manner, engaged with SAP 16) and a free end 45a that is free to move relative to SAP 16. The restrained ends 45b are bonded, attached, adhered, embedded, or otherwise engaged and in contact with outer surface 25 of SAP 16. The free ends 45a are not directly bonded, attached, adhered, embedded, or otherwise engaged (and, in at least some configurations are in not contact with) SAP 16 or the outer surface 25 thereof. The free end of each fiber 21 may be spaced apart from SAP 16 by a distance. The free end of each fiber 21 may be free to move in at least one direction relative to SAP 16. While described as being spaced apart from SAP 16, one skilled in the art would understand that the free ends 45a may have a range of free motion that allows the free ends 45a to contact SAP 16. In some aspects, the free ends 45a are free to move in at least one direction relative to SAP 16, but remain "tethered" to SAP 16 via the restrained ends 45b. As used herein, "free end" refers to an end of a fiber 21 that is not directly attached to the SAP core particle 16 of the fiber-SAP particle 19. Such "free ends" of the fibers 21 are free to move relative to the outer surface 25 of the SAP core particle 16.

In some aspects, the fiber-SAP 19 may include one or more fibers 21b that are at least partially embedded into the SAP 16, providing a path or channel 17 into an interior of SAP 16. Such paths or channels 17 may increase absorption rate for the SAP 16. For example, fiber-SAP 19 shown in FIG. 2 includes at least one fiber, fiber 21b, that is at least partially embedded into the SAP 16 such that at least a portion of fiber 21b extends into an interior of SAP 16, past an outer surface 25 of SAP 16. In some such aspects, liquid, e.g. urine, may absorb into fiber 21b and flow within fiber 21b into an interior 23 of SAP 16.

Regardless of whether or not a fiber is embedded into the SAP, the fibers 21 attached to SAP 16 provide channels for flow of insult (e.g., urine) along the surface of the fibers to the SAP 16 for absorption therein, with the SAP acting as a pump, drawing in liquid from the fibers. In some aspects, an embedded fiber may provide more surface area contact between the SAP and the fiber, enhancing the pulling of insult into the SAP via the fiber. Without being bond by theory, embedding of the fiber may provide a more stable and/or rigid attachment between the fiber and SAP, maintaining the associated fluid flow therebetween in a more consistent and reliable manner.

In some aspects, at least some of the fibers 21 attached to the SAP 16 have at least a portion that extends normal to an outer surface 25 of the SAP 16, or at least has range of free motion relative to SAP 16 such that it is capable of extending normal to an outer surface 25 of the SAP 16. In some aspects, the plurality of fibers 21 extend generally outward from outer surface 25 of SAP 16. Such fiber-SAP particles 19 may be described as a "fuzzy particle" or "hairy particle," with a particle core (i.e., SAP 16) that is bonded, attached, adhered, or otherwise engaged to the plurality of fibers 21 such that free ends of the fibers 21 extend from the SAP 16. In some aspects, the fibers 21 attached to the SAP 16 may have a length that is shorter, equal to, or longer than the average diameter of the SAP 16 particles.

Embedding Mechanisms

As described above in reference to FIGS. 2 and 3, in some aspects at least some of the fibers are embedded into the core SAP particles. The presence of moisture in or on the fiber and/or in or on the SAP at the time of attachment between the fiber and SAP (e.g., within in the mixing zone of the chamber) results in a swelling and/or softening the outer surface of the SAP (i.e., the SAP absorbs the moisture, causing the SAP to swell and soften). The presence of moisture in or on the fiber and/or in or on the SAP also promotes a "stickiness" of both the fiber and SAP, encouraging the fibers and SAP to "stick" together. For example, if the moisture is water, the presence of water in or on the fiber and/or in or on the SAP promotes hydrogen-bonding between the fibers and SAP. Swelling and/or softening of the outer surface of the SAP encourages the fibers to attach thereto. In some aspects, the swelling and/or softening of the SAP is sufficient such that nano- or micro-crevices are formed at the surface of the SAP, such that a portion of the fibers may embed within these crevices and attach with the SAP. Subsequent drying of the fibers and SAP results in a corresponding shrinking and/or hardening of the SAP; thereby, holding the fibers in place on and/or embedded within the SAP. Such embedded fibers penetrate at least some distance into the SAP, past the outer surface of the SAP.

In some aspects, each fiber-SAP particle has from 10 to 60 weight percent fibers attached thereto, or from 20 to 50 weight percent fibers attached thereto, or from 30 to 40 weight percent fibers attached thereto, each based on the total weight of the fiber-SAP particle. In certain aspects, each fiber-SAP particle has from 0.1 to 30 wt % of fiber or from 0.5 to 15 wt % of fiber based on the total weight of the fiber-SAP particle.

Fiber-SAP Particle Interaction

Figure 3:
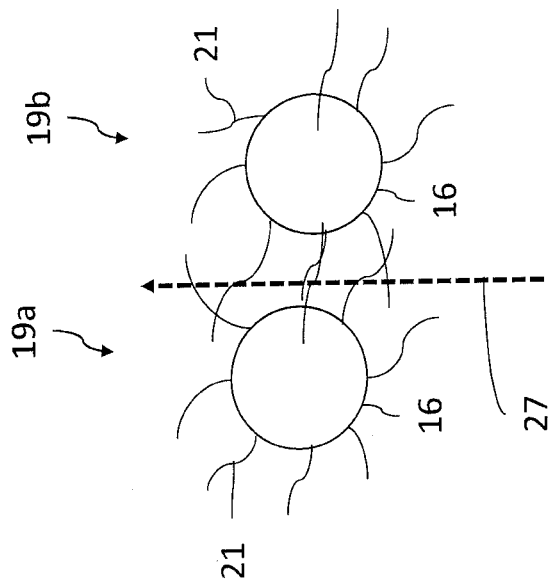
FIG. 3 is a simplified illustration of two adjacent fiber-SAP particles in accordance with certain aspects of the present disclosure.

With reference to FIG. 3, adjacent fiber-SAP particles 19a and 19b may remain at least partially spaced apart, such that one or more fibers 21 of the adjacent fiber-SAP particles 19a and 19b may be in contact or entangled with one another. In some aspects, one or more fibers 21 of the adjacent fiber-SAP particles 19a and 19b may be bonded (e.g., H-bonded) with one another. In other aspects, fibers 21 of adjacent fiber-SAP particles 19a and 19b are not in contact, entangled with, or bonded with one another. In some aspects, the SAP 16 of the adjacent fiber-SAP particles 19a and 19b are not in contact. In other aspects, the SAP 16 of the adjacent fiber-SAP particles 19a and 19b are in contact. In some aspects, fibers 21 of fiber-SAP particles 19a and 19b may maintain adjacent fiber-SAP particles 19a and 19b at least partially spaced apart, forming wicking paths 27 between the adjacent fiber-SAP particles 19a and 19b. The wicking paths 27 may allow for fluid flow there-between, which may improve fluid distribution amongst fiber-SAP particles. When incorporated into an absorbent core, the entanglement and/or rigidity of fibers 21 may promote immobilization of fiber-SAP particles therein, promoting the formation of such wicking paths.

Network of Fiber-SAP Particles

FIG. 3A depicts an exemplary network 119 of fiber-SAP particles 19a. As shown, the network 119 may include one or more fiber-SAP particles having fibers that are entangled with fibers of adjacent fiber-SAP particles (e.g., 19d), as well as one or more fiber-SAP particles having fibers that are not entangled with fibers of adjacent fiber-SAP particles (e.g., 19c).

Absorbent Core

Figure 7:
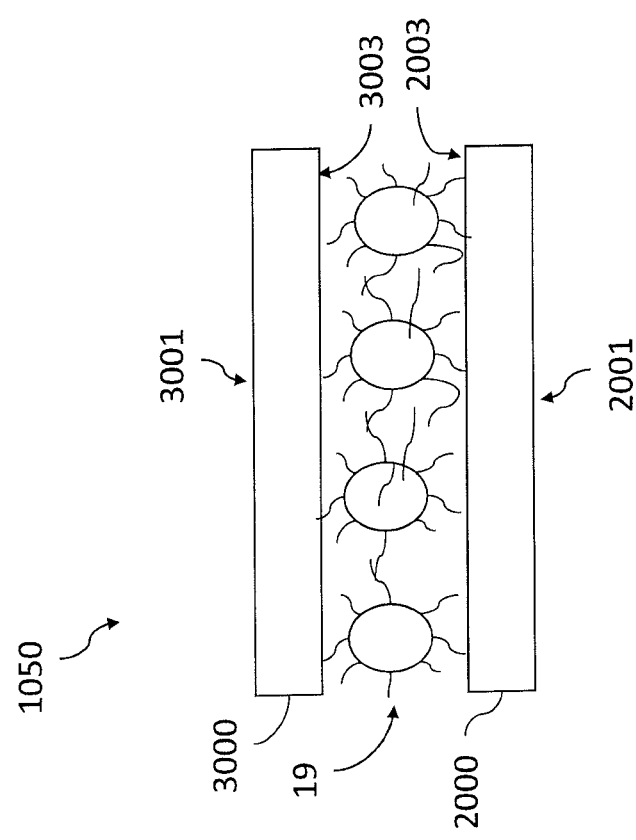
FIG. 7 is a simplified illustration of an absorbent core in accordance with certain aspects of the present disclosure.

With reference to FIG. 7, the fiber-SAP particles 19 may be deposited onto a substrate 2000, such as a non-woven (e.g., a bulky non-woven). A cover layer 3000, such as a non-woven or bulky non-woven, may be placed above the substrate 2000, such that the fiber-SAP particles 19 are positioned between an outer surface 2001 of the substrate 2000 and an outer surface 3001 of the cover layer 3000, and between an inner surface 2003 of the substrate 2000 and an inner surface 3003 of the cover layer 3000, forming absorbent core 1050.

Absorbent Articles

The fiber-SAP particles 19 may be incorporated into an absorbent core and/or an absorbent article, such as into an absorbent core of a diaper. In some aspects, the fiber-SAP particles 19 may be used in combination with conventional SAP (i.e., non-fiber-SAP) without fibers 21 thereon. For example, with reference to FIG. 4, an absorbent core 1050 of a diaper 1000 may include one or more sections, pockets, zones, stripes, lanes, or combinations thereof that contain fiber-SAP particles, zone 1019, and one or more sections, pockets, zones, stripes, lanes, or combinations thereof that contain non-fiber-SAP and do not contain fiber-SAP particles, zones 1030a and 1030b. Absorbent core 1050 may be incorporated into chassis 1051 of diaper 1000 by any method, including those methods well known to those skilled in the art.

During use of an article containing fiber-SAP particles 19, such as a diaper incorporating such fiber-SAP particles, the fibers 21 attached to SAP 16 may act as shock absorbers for the SAP 16 cores, resulting in less compression of the SAP 16 cores; thereby, maintaining swellablity of the SAP 16.

Methods of Making Fiber-SAP and Absorbent Cores and Articles Including the Same

Figure 4:
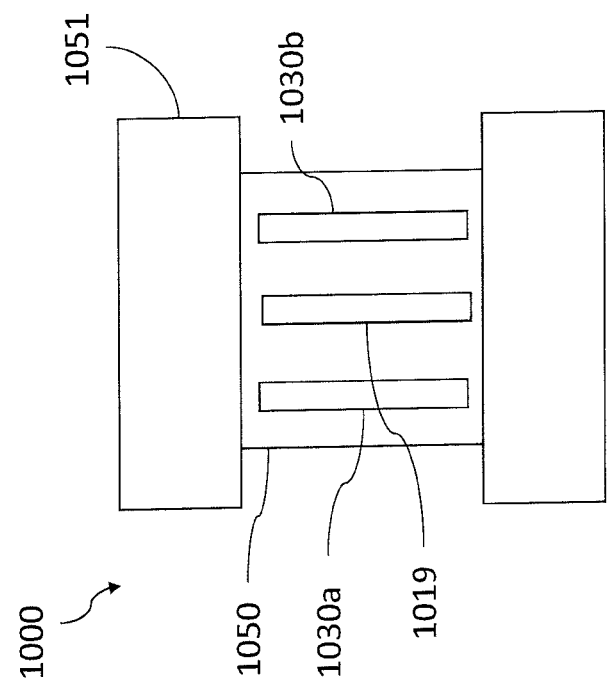
FIG. 4 depicts a diaper in accordance with certain aspects of the present disclosure.
Figure 5A:
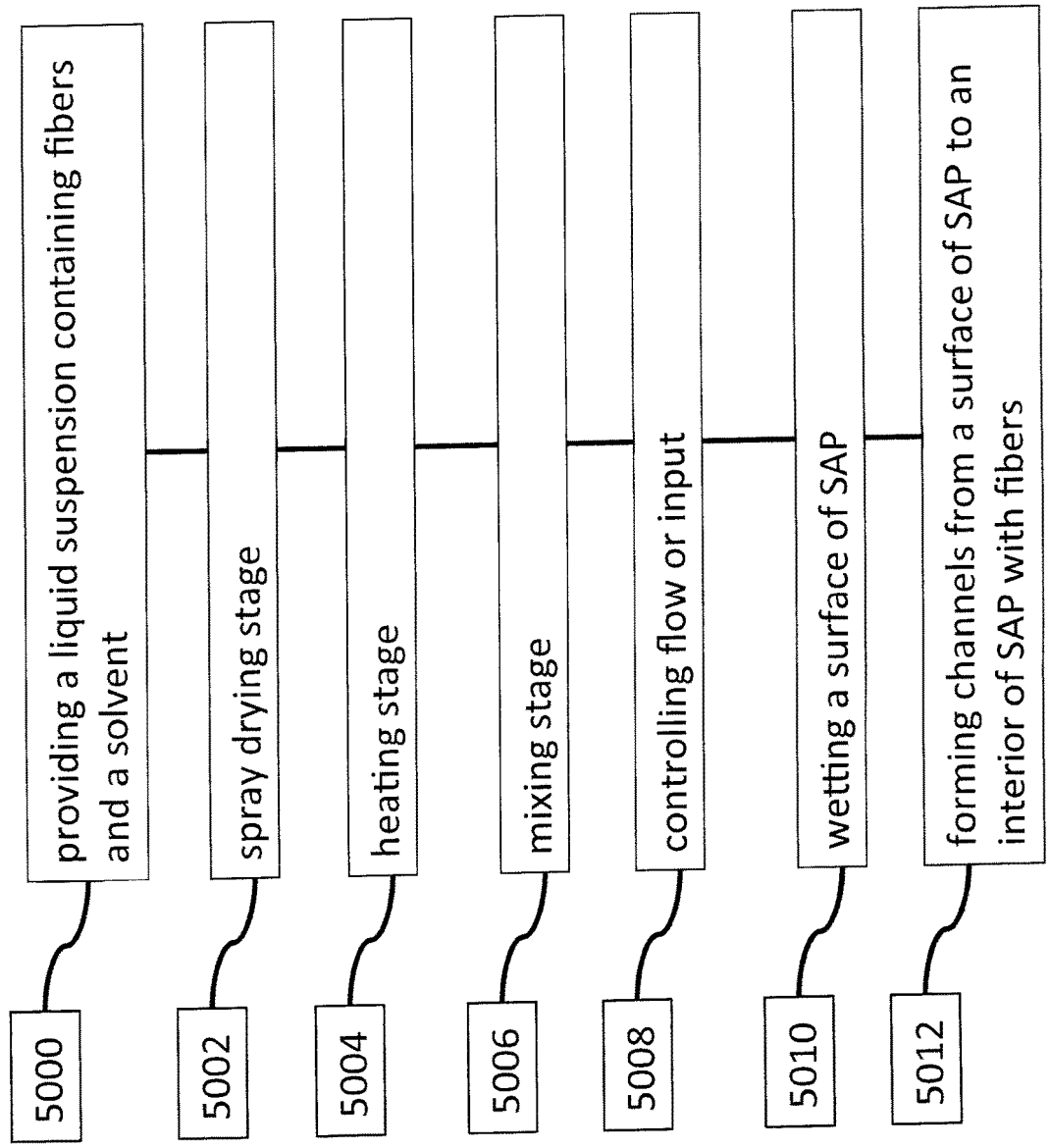
FIGS. 5A and 5B are a flow chart of a method of making fiber-SAP particles in accordance with certain aspects of the present disclosure.
Figure 5B:
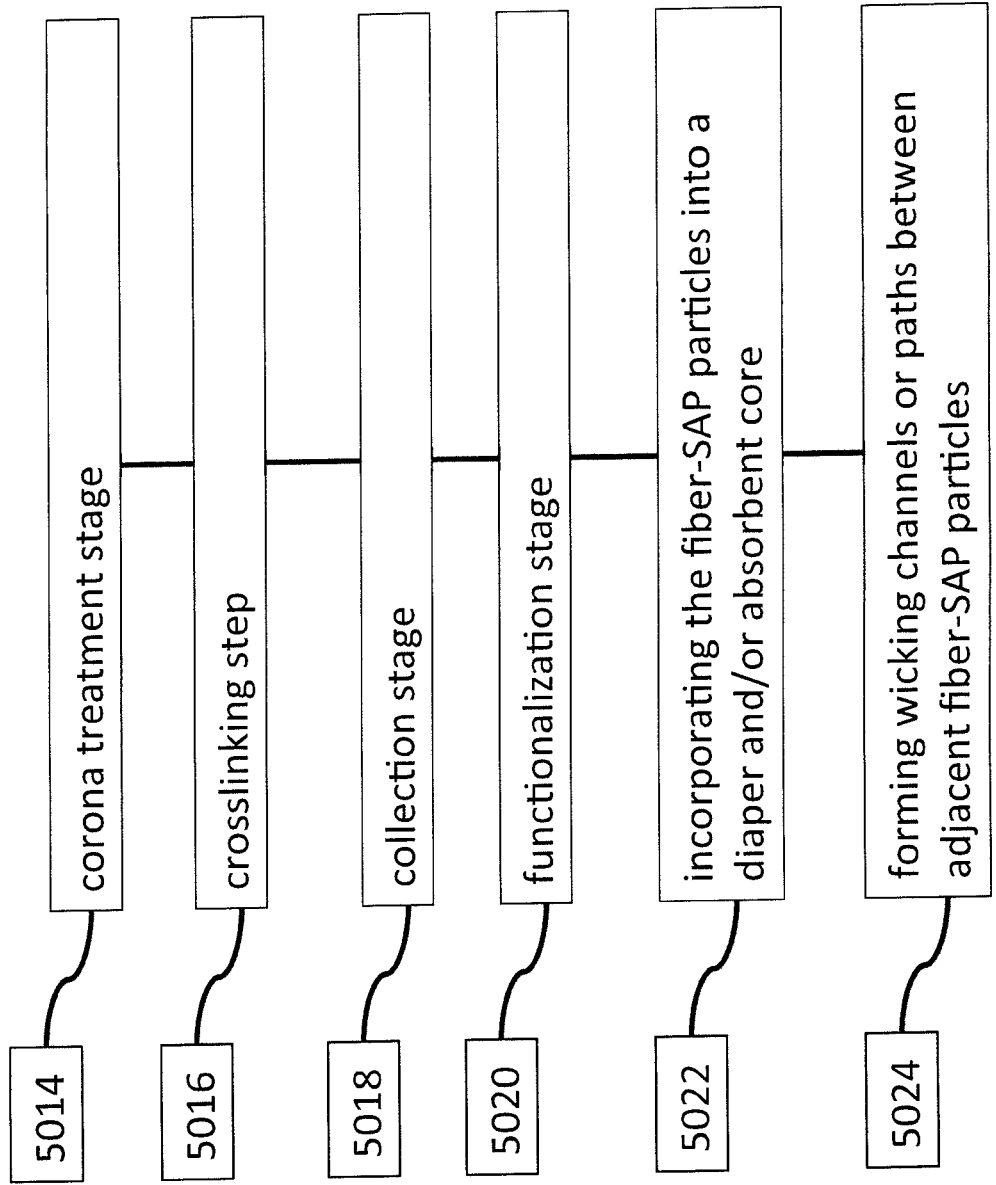

FIG. 5 is a flow chart of a method in accordance with certain aspects of the present disclosure. The method of FIG. 5 may be implemented using systems and/or apparatus depicted in FIGS. 1, 1A, 8A, 8B, 10A, and 10B to form one or more fiber-SAP particles 19 as depicted in FIG. 2, 2A, 2B, 3, or 3A and/or diapers 1000 as depicted in FIG. 4 and/or absorbent cores 1050 as depicted in FIG. 7.

The method may include providing a liquid suspension containing fibers and a solvent, 5000. For example, the liquid suspension may be a slurry of MFC, NFC, or combinations thereof in water and/or ethanol.

The method may include a spray drying stage, in which the liquid suspension is spray dried into a fluidized bed chamber (e.g., chamber 24 of apparatus 100), 5002.

In some aspects, the method may include a heating stage, in which the liquid suspension is spray dried into a heated environment or zone of the fluidized bed chamber, 5004. For example, the heated zone 31 may be heated to a temperature above the ambient temperature surrounding apparatus 100, such as above room temperature (i.e., above 20 degrees Celsius).

The method may include a mixing stage, in which SAP, or a SAP and additives, are introduced into the fluidized bed chamber and mixed with the fibers of the liquid suspension to form fiber-SAP particles, in which the fibers are adhered and/or bonded with the SAP particles, 5006. While SAP 16 and additives 18 are shown as being introduced separately in FIG. 1, SAP 16 and additives 18 may be mixed prior to entry into the chamber 24 of apparatus 100. Also, while the liquid suspension and additives 18 are shown as being introduced separately in FIG. 1, the liquid suspension and additives 18 may be mixed prior to entry into the chamber 24 of apparatus 100. In the mixing stage, turbulence and/or heat may be utilized to mix and initiate interaction between SAP 16, fibers 21 of the liquid suspension, and any additives present to form fiber-SAP particles 19.

In some aspects, the method includes controlling flow or input, 5008, of the spray dried fibers 21, the SAP 16, and any additives 18, thereby controlling the chemical and/or physical properties of the resulting fiber-SAP particles 19.

In some aspects, the method includes wetting a surface of SAP, 5010, within the chamber of the apparatus. Wetting of the surface of the SAP 16 may be accomplished by vapor formed from spray drying the liquid suspension, by introduction of vapor into the chamber 24 of the apparatus 100, or combinations thereof. As described previously, wetting the surface of the SAP 16 may promote adhesion and/or bonding of fibers 21 to the surface of the SAP 16. In some aspects, the surface of SAP 16 is pre-wet prior to introduction into chamber 24.

The method may include forming channels from a surface of SAP to an interior of SAP with fibers, 5012. For example, as described above, fibers 21 may become at least partially embedded into the SAP 16 during interaction therewith.

The method may include a corona treatment stage, 5014 in which a corona discharge plasma is used to modify the surface of SAP, fiber, and/or fiber-SAP particles.

The method may include a crosslinking step, 5016, in which the surface of the SAP and/or the fiber-SAP particles are subjected to at least partially crosslinking. The crosslinking step may be prior to, coincident with, or subsequent to the corona treatment stage.

The method may include a collection stage, 5018, in which the fiber-SAP particles are collected, and an optional additional drying stage in which the fiber-SAP particles are dried.

In some aspects, the method may include functionalizing the fiber, SAP, fiber-SAP, or combinations thereof in a functionalization stage 5020. Functionalization of the fiber 21 and/or SAP 16 may occur within or upstream of the fluidized bed chamber. Functionalization of the fiber-SAP 19 may occur within or downstream of the fluidized bed chamber. For example, the fiber 21, SAP 16, and/or fiber-SAP 29 may be functionalized using metal ions for antibacterial and odor reducing properties; polyelectrolyte complexes that can add cation exchange capabilities; other functional additives, such as for biosensing; clay bentonite particles; and cross linking particles. In some aspects, the fiber and/or SAP particles are functionalized prior to introduction into the chamber.

The method may include incorporating the fiber-SAP particles into a diaper and/or absorbent core, 5022. For example, the fiber-SAP may form a portion of an absorbent core 1050 of the diaper 1000.

The method may include forming wicking channels or paths between adjacent fiber-SAP particles, 5024, within the absorbent core. For example, the fiber-SAP particles 19 may be deposited such that adjacent fiber-SAP particles 19 are at least partially spaced apart.

One or more steps described with reference to FIG. 5 may be eliminated. Also, additional steps not set forth in FIG. 5 may be included in the method. Furthermore, the steps of the method are not limited to the particular order, as shown in FIG. 5, and may occur in an order not shown in FIG. 5.

FIG. 6 is a flow chart of a method in accordance with certain aspects of the present disclosure. The method of FIG. 6 may be implemented using system and/or apparatus depicted in FIGS. 1, 1A, 8A, 8B, 10A, and 10B to form one or more fiber-SAP particles 19 as depicted in FIG. 2, 2A, 2B, 3, or 3A and/or diapers 1000 as depicted in FIG. 4 and/or absorbent cores 1050 as shown in FIG. 7.

The method may include providing a liquid suspension containing fibers and a solvent, 6000.

The method may include spray drying stage, 6002, in which the liquid suspension is spray dried into a fluidized bed chamber (e.g., chamber 24 of apparatus 100).

The method may include a mixing stage, 6004, in which SAP, or a SAP and additives, are introduced into the fluidized bed chamber and mixed with the fibers of the liquid suspension to form fiber-SAP particles, in which the fibers are adhered and/or bonded with the SAP particles.

The method may include a collection stage, 6006, in which the fiber-SAP particles are collected, and an optional additional drying stage in which the fiber-SAP particles are dried.

The method may include incorporating the fiber-SAP particles into a diaper and/or absorbent core, 6008.

One or more steps described with reference to FIG. 6 may be eliminated. Also, additional steps not set forth in FIG. 6 may be included in the method. Furthermore, the steps of the method are not limited to the particular order, as shown in FIG. 6, and may occur in an order not shown in FIG. 6.

Figure 6A:
FIG. 6A is a flow chart of a method of making fiber-SAP particles in accordance with certain aspects of the present disclosure.

FIG. 6A is a flow chart of a method in accordance with certain aspects of the present disclosure. The method of FIG. 6A may be implemented using system and/or apparatus depicted in FIGS. 1, 1A, 8A, 8B, 10A, and 10B to form one or more fiber-SAP particles 19 as depicted in FIG. 2, 2A, 2B, 3, or 3A and/or diapers 1000 as depicted in FIG. 4 and/or absorbent cores 1050 as shown in FIG. 7.

The method may include at least partially drying fibers of a liquid suspension of fibers and a solvent. This partial drying may be performed via atomization of the liquid suspension.

The method may include a mixing stage, in which SAP is mixed with the at least partially pre-dried fibers of the liquid suspension to form fiber-SAP particles. In some aspects the SAP is pre-wet prior to mixing, such as via deposition of moisture dried from the fibers. The method of FIG. 6A may be combined with any one or more of the steps shown and described with reference to FIGS. 5A, 5B, 6, and 9.

Electrostatic Charging

In some aspects, the fiber-SAP particles 19 are subjected to electrostatic charging. Such electrostatic charging may be performed within chamber 24, within collection zone 26, or downstream of both chamber 24 and collection zone 26. Electrostatic charge causes the free ends of the fibers to raise and extend outwards from the outside surface 25 of the SAP 16 core particle. Thus, the electrostatic charging may increase the "fuzziness" of the fiber-SAP particles 19 by "lifting" the free ends of the fibers away from the SAP 16 surface to extend outward therefrom.

Relative Dimensions of Fiber and SAP

In some aspects, the relative dimensions of the SAP core particle 16 to those of the fibers 21 are selected to eliminate or at least minimize the occurrence of wrapping of the fibers 21 around the SAP 16.

Opening and Closing of Crevices

Figure 2A:
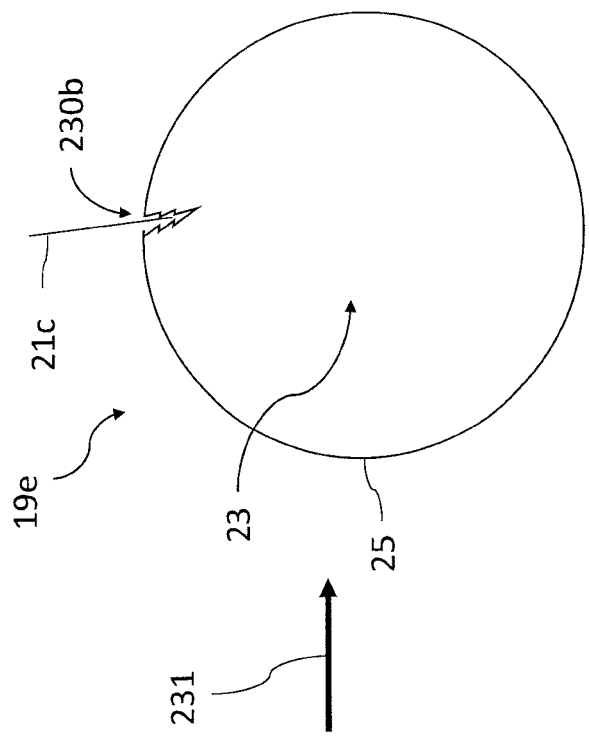
FIG. 2A is a simplified illustration of a swollen fiber-SAP particle in accordance with certain aspects of the present disclosure.
Figure 2B:
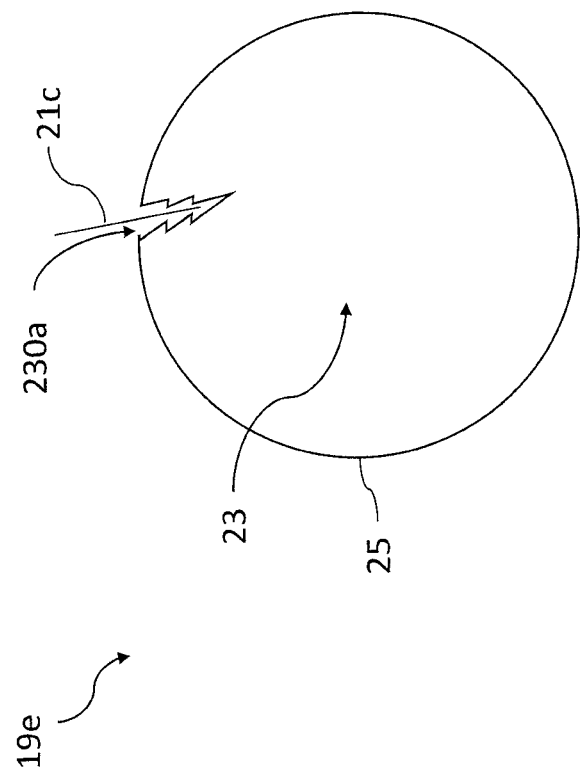
FIG. 2B is a simplified illustration of the fiber-SAP particle of FIG. 2A after drying in accordance with certain aspects of the present disclosure.

With reference to FIGS. 2A and 2B, a fiber-SAP particle 19e is shown before drying and after drying. Upon wetting of the SAP core particle, the SAP swells. Any crevices that are present on the outer surface 25 of the SAP particle will expand upon swelling of the SAP. FIG. 2A shows crevice 230a in a swollen state. This opening or expanding of the crevice 230a allows fibers, such as fiber 21c to more readily fit into crevice 230a. This embedding of fiber 21c into crevice 230a may occur, for example, within the mixing zone 33. Upon subsequent drying of the fiber-SAP particle 19e, drying 231, the fiber-SAP particle 19e shrinks and the crevices on the outer surface 25 correspondingly shrink. Thus, as shown in FIG. 2B, crevice 230b is relatively closed in comparison to the same crevice when the fiber-SAP particle 19 is in the swollen state. Such closing of SAP crevices about fibers may stabilize the attachment of the fiber 21c with the core SAP particle by promoting further interaction (e.g., H-bonding, polymer entanglement, etc,) between the fiber 21c and the core SAP particle, thus strengthening the bond(s) therebetween. In some aspects, the relative closing of the crevice about the fiber entraps the fiber therein. In some aspects, the fibers are selected to have a diameter that corresponds with the width of the crevices in the SAP outer surface 25, such that the diameter of the fibers are capable of fitting within crevice, at least when the crevice is in the swollen state.

Figure 2D:
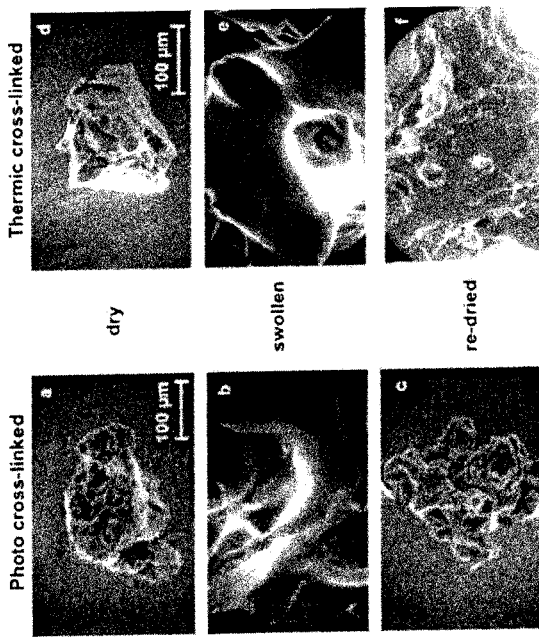
FIGS. 2C and 2D are example scanning electron microscope (SEM) images of SAP.
Figure 2C:
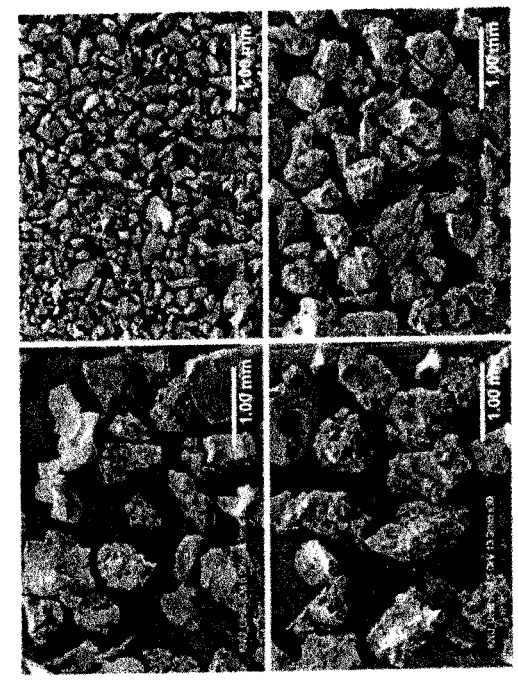

FIG. 2C is an SEM of SAP (solution polymerized) having an irregular surface, including rugosities and crevices on the surface thereof. FIG. 2D are SEMs of photo and thermic crosslinked SAP in dry, fully swollen, and redried states. In some aspects of the present disclosure, the SAP is does not become full swollen, but is partially swollen.

Process/System Zones

With reference to FIG. 8A, certain aspects of the processes, systems, and apparatus described herein are discussed. System 800 includes multiple zones within which different steps of the process may be carried out. First zone 801 is an introduction zone in which the liquid suspension in provided. Within first zone 801, the liquid suspension is atomized to form an aerosol thereof. In some aspects, the first zone 801 is devoid of SAP.

Second zone 802 is a pre-drying zone in which at least some of the liquid of the liquid suspension is flashed off of the fibers and into the surrounding environment. Partial drying of the fibers may allow for more dynamic movement of the fiber within system 800, as the fibers are lighter in a dried state. In some aspects, the liquid flashed off of the fibers flows into contact with SAP prior to the fiber contacting the SAP. As the liquid has flashed off into a vapor, the vapor spreads throughout system 800, and the fibers are maintained in a relatively suspended state within the air in system 800 due to the turbulent air flow patterns within system 800. This vapor may deposits onto the SAP, resulting in pre-wetting of the SAP. Such prewetting of the SAP results in at least partial swelling of the SAP, making the SAP conducive to attachment with fibers (e.g., such that fibers may become embedded therein). In some aspects, the second zone 802 is devoid of SAP.

Third zone 803 is a SAP introduction zone. While the SAP introduction zone 803 is shown as downstream of (i.e., subsequent to) the liquid suspension introduction zone 801 and the pre-drying zone 802, system 800 is not limited to this particular arrangement.

Fourth zone 804 is a mixing zone, within which the SAP, fibers, vapor, and air turbulently mix together. Within mixing zone 804, each of the SAP, fibers, vapor, and air are maintained in a suspended state, under turbulent conditions, to promote mixing and interaction therebetween. While shown as separate, fourth zone 804 may be coincident with third zone 803. In some aspects, agitation within the mixing zone is sufficient that fibers interacting with SAP that is not swollen may become detached from the un-swollen SAP, and may subsequent attach to swollen SAP.

Fifth zone 805 is an optional reaction zone in which one or more chemical reactions or other modification methods may be used to modify the SAP, fibers, fiber-SAP particles, or combinations thereof. While shown as downstream of the mixing zone 804, the reaction zone may be coincident with or upstream of the mixing zone. In some aspects, the reaction zone 805 is a Corona treatment zone and/or an electrostatic charging zone.

Sixth zone 806 is a drying zone. Within drying zone 806, fibers, SAP, fiber-SAP particles, or combinations thereof undergo drying, such as via heat, air flow, residence time, or combinations thereof. While shown as downstream of the mixing zone 804 and optional reaction zone 805, the drying zone may be coincident with or upstream of the mixing zone 804 and/or optional reaction zone 805.

Seventh zone 807 is a collection zone in which the fiber-SAP particles, optionally in combination with fibers and/or SAP, are collected. While shown as downstream of the drying zone 806, the collection zone may be coincident with the drying zone.

With reference to FIG. 8B, certain aspects of the processes, systems, and apparatus described herein are discussed. System 800b includes multiple zones within which different steps of the process may be carried out.

Zone 810 is a pre-drying zone in which at least some of the liquid of the liquid suspension is flashed off of the fibers and into the surrounding environment. Partial drying of the fibers may allow for more dynamic movement of the fiber within system 800b, as the fibers are lighter in a dried state. In some aspects, the liquid flashed off of the fibers flows into contact with SAP prior to the fiber contacting the SAP. As the liquid has flashed off into a vapor, the vapor spreads throughout system 800b, and the fibers are maintained in a relatively suspended state within the air in system 800b due to the turbulent air flow patterns within system 800b. This vapor may deposits onto the SAP, resulting in pre-wetting of the SAP. Such prewetting of the SAP results in at least partial swelling of the SAP, making the SAP conducive to attachment with fibers (e.g., such that fibers may become embedded therein). In some aspects, the zone 810 is devoid of SAP.

Zone 812 is a mixing zone, within which the SAP, fibers, vapor, and air turbulently mix together. Within mixing zone 812, each of the SAP, fibers, vapor, and air are maintained in a suspended state, under turbulent conditions, to promote mixing and interaction therebetween.

Any one or more of the zones shown and described in FIG. 8A may be used within system 800b.

While each zone is shown in FIGS. 8A and 8B as being a separate and distinct zone, in some aspects one or more of the zones are coincident with one another. Also, while each zone is shown in FIGS. 8A and 8B as being within a single system, in some aspects one or more of the zones are in a separate system(s) from the other zones.

In some aspects, the residence time within each zone is controlled. In some aspects, one or more of the zones may selectively isolated from adjacent zones of the system, such that fluid communication between the zones is selectively controlled. Some mechanisms used to control residence time and rate of input of constituents include the use of intermittent spray drying (or other liquid suspension introduction method), control of size of zones and/or chambers, control of opposing air flows with the system, and the positioning of one or more of the zones within a separate chamber.

Figure 9:
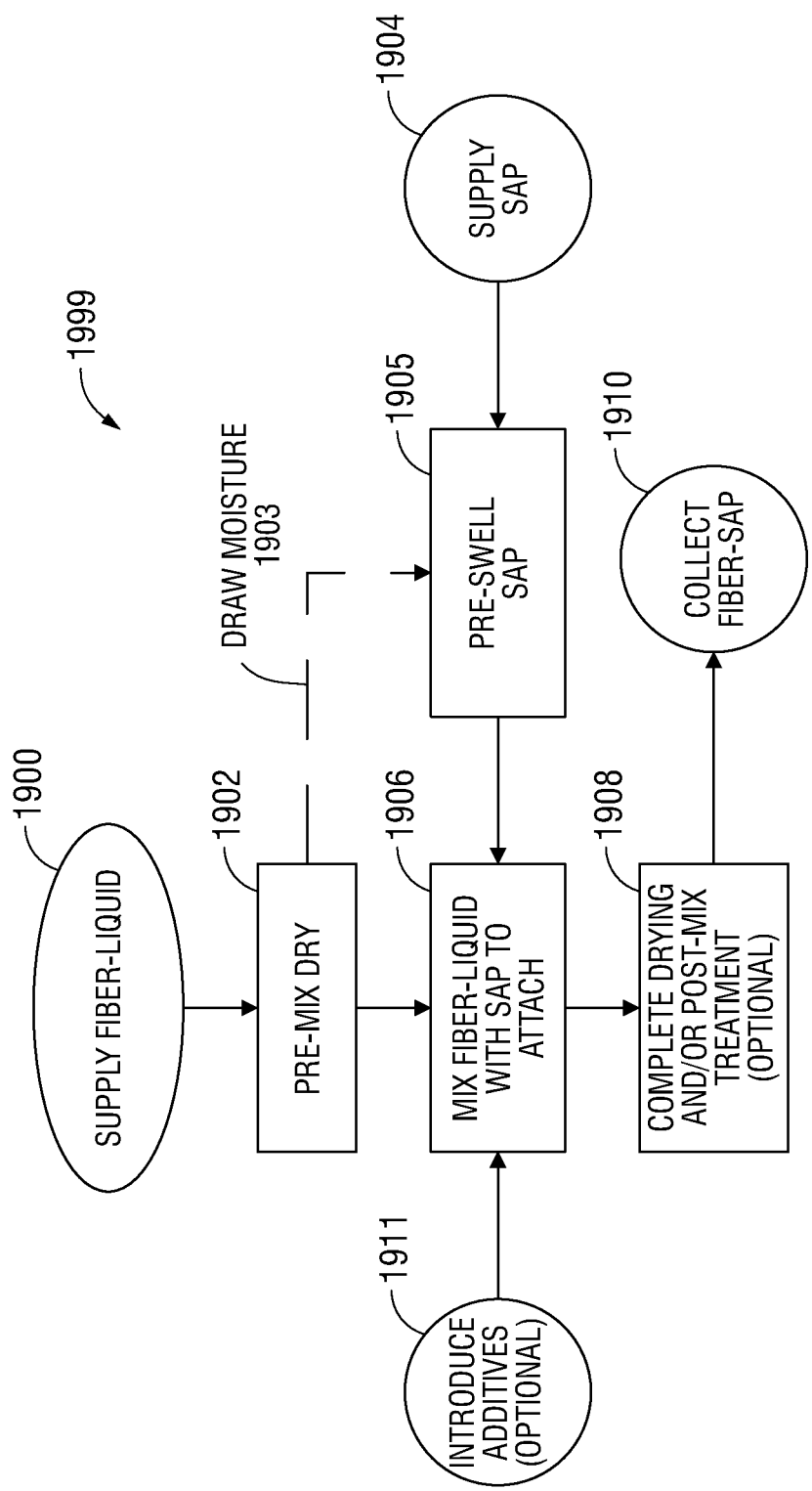
FIG. 9 is a flow schematic of a method of making fiber-SAP particles in accordance with certain aspects of the present disclosure.

FIG. 9 depicts a schematic of the method accordance with certain aspects of the present disclosure. As shown in FIG. 9, a liquid suspension of fibers is supplied, step 1900. The liquid suspension of fibers is subjected to a pre-mixing drying stage, step 1902. In step 1902, the fibers of the liquid suspension of fibers are at least partially dried via formation of an aerosol of the liquid suspension, dispersing the liquid and fibers in air or another gaseous medium.

Optionally, at least some of the liquid dispersed and/or dried from the fibers in step 1092 may be directed into contact with SAP, step 1903. SAP is supplied via a SAP supply source, step 1904, optionally to a SAP pre-swell zone at step 1905 for pre-wetting of the SAP. This pre-wetting of the SAP activates the surface of the SAP for attachment with the fibers by swelling and softening the SAP.

In step 1906, the pre-wet SAP (or optionally dry SAP), is mixed with the partially dried fibers from step 1902. The mixing of the SAP with the fibers results in attachment of the fiber with the SAP, forming fiber-SAP particles.

Optionally, in step 1908 the fiber-SAP particles are further dried.

Optionally, in step 1910 the fiber-SAP particles are collected.

Optionally, additives are introduced at step 1911.

Any one or more of the steps described with reference to FIGS. 5A, 5B, 6, and 6A may be combined with the steps described with reference to FIG. 9.

Figure 10A:
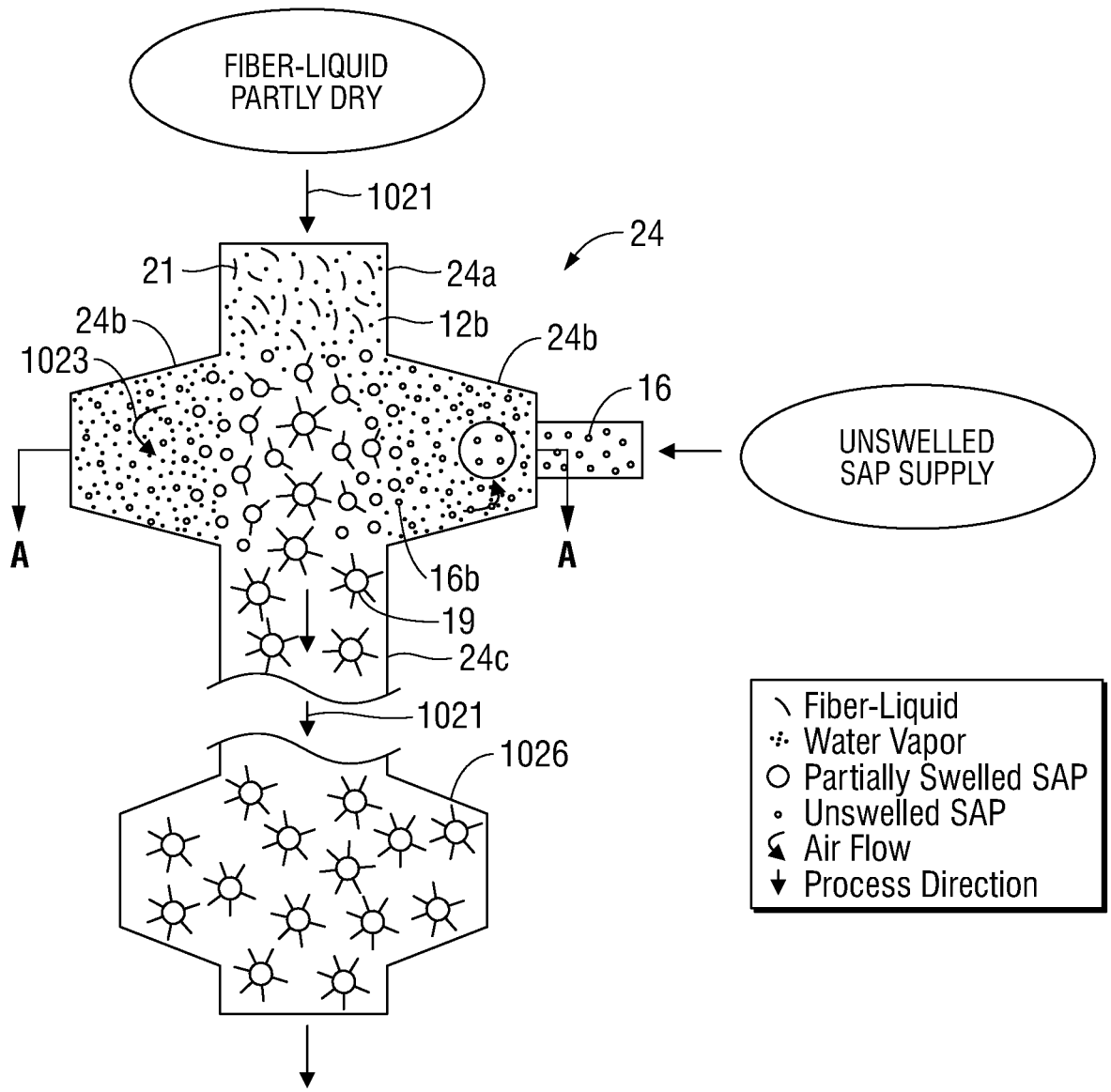
FIG. 10A is a schematic of an apparatus for making fiber-SAP particles in accordance with certain aspects of the present disclosure.
Figure 10B:
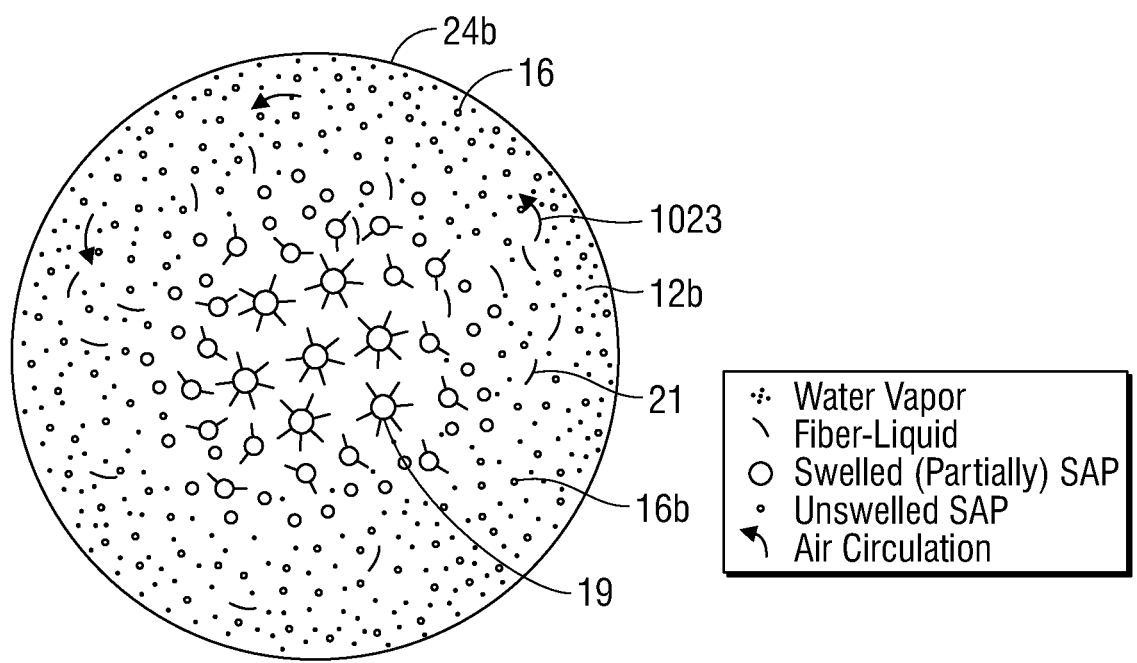
FIG. 10B is a cross-sectional view along line A-A of FIG. 10A.

FIG. 10A depicts a schematic of an apparatus for attaching fibers with SAP, in accordance with certain embodiments, and FIG. 10B depicts a cross-sectional view thereof along line A-A. Chamber 24 may include expanded section 24b that is of a greater cross-sectional area than the upper portion of chamber 24a. The liquid suspension of fibers is introduced into the chamber upstream of expanded section 24b and flows downward into the expanded section 24d. Upon entry into expanded section 24b, the fibers have been at least partially dried, as described elsewhere herein. Thus, fibers 21 and vapor 12b flow into expanded section. SAP 16 is introduced into the expanded section 24b outside of the central flow channel 1021 of chamber 24. While fibers 21 are directed, such as via gravity, to at least substantially flow along the central flow channel 1021 of chamber 24, vapor 12b is less affected by gravity and is free to flow as a fluid through chamber 24 (e.g., fluid flow path 1023) including into expanded section 24b. As such, SAP 16 and vapor 12b mix within expanded section 24b prior to the mixing of SAP 16 with fibers 21, or at least prior to substantial mixing of SAP 16 with fibers 21 within the central flow channel 1021. Thus, pre-wet, partially swollen SAP 16b may contact fibers 21 within the central flow channel 1021 to form fiber-SAP particles 19, which are directed out of chamber 24 via exit 24c and optionally into a further drying zone and/or collection zone 1026.

As shown in FIG. 10B, along the perimeter of the expanded section 24b, the SAP is swollen, as the SAP circulates and flows within the expanded section 24b and moves close the central flow channel, the SAP 16 becomes increasingly swollen via contact with vapor and deposition thereof. Thus, when the SAP reaches the central flow channel and contacts the fibers, the SAP is pre-wet and pre-swollen (and thus activated for contact and attachment with fiber), for formation of fiber-SAP particles 19.

One skilled in the art would understand that other arrangements and configurations may be used to provide for the pre-wetting of the SAP with the liquid evaporated from the fiber prior to contact between the SAP and the fiber. Also, one skilled in the art would understand that the schematic of FIGS. 10A and 10B is not to scale, and is for illustrative purposes only.

Figure 11:
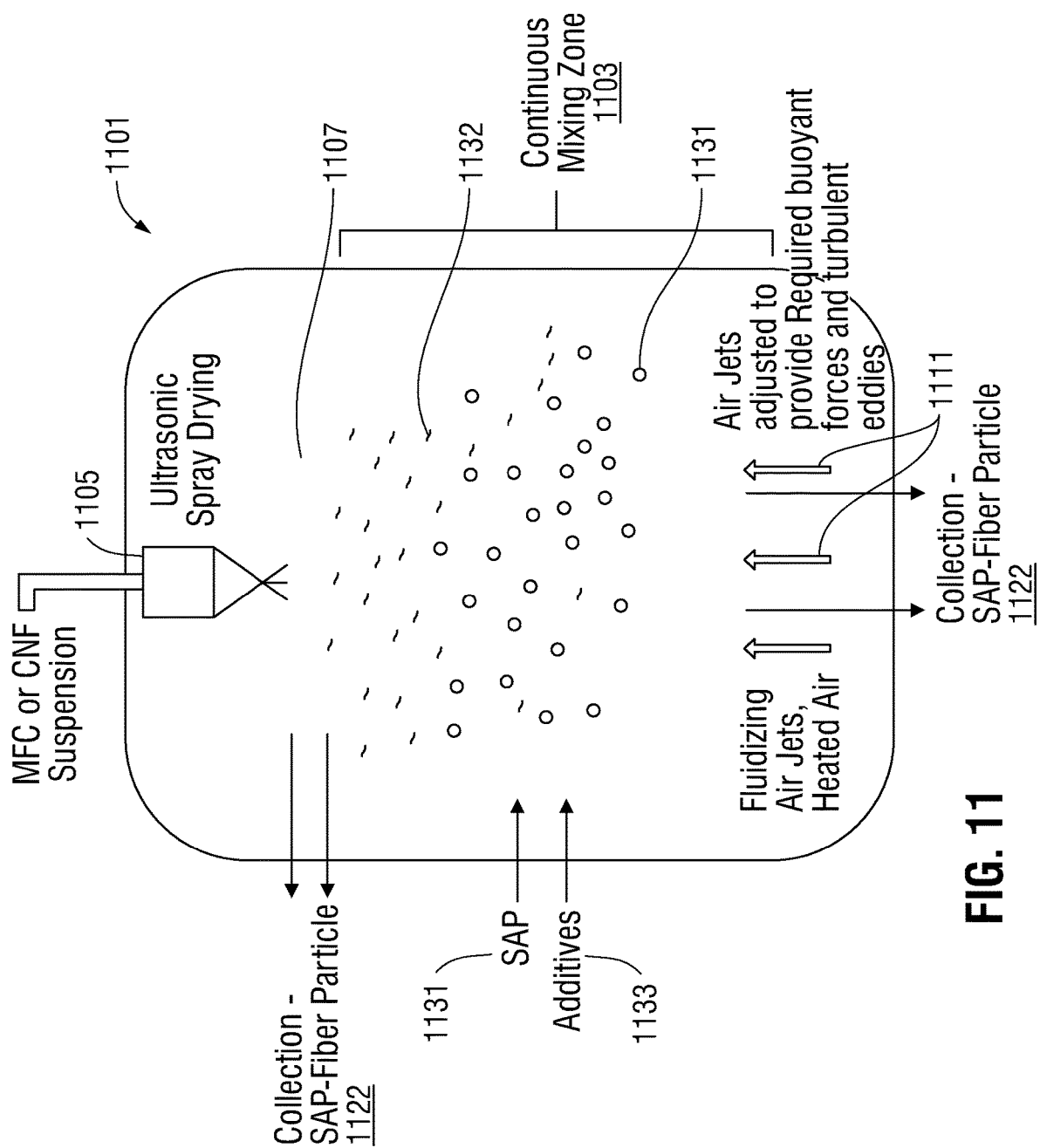
FIG. 11 is a schematic of an apparatus for forming fiber-SAP particles, indicating flow paths for various inputs and outputs, including air jet flow paths.

Referring to FIG. 11, in another aspect of the disclosure, a schematic of an exemplary system 1101, apparatus 1101 and process/method 1101 are shown for forming fiber-attached (preferably embedded) SAP particles. The system or apparatus 1101 includes a mixing zone or chamber 1103 in which SAP 1131, desired additives 1133, and partially spray dried fibers 1134 (with liquid supported thereon) particles are presented together for mixing. The fibers are introduced via a spray drying device 1105 directing a liquid suspension of the fibers into the apparatus 1101. The mixing zone 1103 typically holds fiber-Sap particles of varying dryness. These particles are suspended and sometimes circulated in the mixing zone 1103 before being passed on.

This simplified diagram depicts two outlets or collection points 1122 for Fiber-attached (preferably embedded) SAP particles. In this example, fluidizing air jets 1111 are employed with (or without) a heating element to convey heat to the mixing dynamics (in preferred mixing zone 1103) and facilitate further drying. The air jets 1111 may be adjusted (controlled) to present the required buoyant forces (to suspend the fiber-sap mix) in the mixing zone and also to generate turbulent eddies. Depending on whether the desired finished particle (dry) is heavier or lighter than the buoyant force generated by the air jets 1111 determines the outlet 1122 through which the finished fiber-sap particle may be collected or communicated to the next stage (e.g., a treatment stage such as corona treatment or crosslinking, or collection).

In further variations an employment of fluidized bed technology, the fiber-Sap mixture may be circulated to generate centrifugal forces which help separate particles between two (or more) degrees of dryness. In certain variations, dryer particles are separated and/or isolated and passed out from the mixing chamber while other or remaining particles are subjected to further residence time, circulation, and/or drying, or re-directed and/or recirculated in the system for forming fiber-SAP particles. In one application, a cyclone device may be employed to act on the fiber-SAP particles, which may then be separated by angular velocities. In any event, it is one aspect and advantageous feature of the described apparatus, systems, and methods that a target final product may be identified or isolated by recognizing and manipulating the balance of forces between (among) buoyant force, drag, weight and others such as centrifugal forces. In specific examples, attention is directed to the difference in basic properties such as weight and surface area between starting and finished fiber-sap particle products to facilitate collection and separation of finished products.

The foregoing description has been presented for purposes of illustration and description. It is to be noted that the description is not intended to limit the embodiments to the various articles, products, systems, apparatus, and processes disclosed herein. Various aspects of the embodiments as described above may be applicable to other types of disposable absorbent articles and garments, and processes for making the same. For example, the absorbent composite, and its method of manufacture, as described above, may be incorporated in other products and methods of manufacture. Moreover, the processes described herein may be utilized to produce compositions, garments and articles other than those described herein. Such variations of the embodiments will become apparent to one skilled in the relevant consumer products are provided with the present disclosure. Consequently, variations and modifications commensurate with the above teachings, and the skill and knowledge of the relevant art, are within the scope of the present disclosure. The embodiments described and illustrated herein are further intended to explain the best modes for practicing the embodiments, and to enable others skilled in the art to utilize the embodiments, with various modifications required by the particular applications or uses of the present embodiments. Furthermore, the claims following this description is provided to articulate, or elaborate on, some of the different aspects of the methods and products (compositions). These claims are intended to form and describe additional aspects and features of, and important, to the present disclosure.

What is claimed is:

1. A fiber-SAP particle comprising:
   a superabsorbent core particle; and
   a plurality of fibers attached to the superabsorbent core particle, wherein at least one of the fibers is at least partially embedded into the superabsorbent core particle; and
   wherein the fibers comprise fibrillated fibers.

2. The fiber-SAP particle of claim 1, wherein the plurality of fibers extend from an outer surface of the superabsorbent core particle.

3. The fiber-SAP particle of claim 1, wherein at least some of the fibers have a first end that is attached to the superabsorbent core particle and a second end that is free to move relative to the superabsorbent core particle.

4. The fiber-SAP particle of claim 1, wherein the fibers are adhered to the superabsorbent core particle, hydrogen bonded to the superabsorbent core particle, entangled with polymer chains of the superabsorbent core particle, or combinations thereof.

5. The fiber-SAP particle of claim 1, wherein at least a portion of at least some of the fibers extend from the superabsorbent core particle, normal to an outer surface of the superabsorbent core particle.

6. The fiber-SAP particle of claim 1, wherein the at least one fiber that is at least partially embedded into the superabsorbent core particle penetrates a distances past an outer surface of the superabsorbent particle and into an interior of the superabsorbent particle.

7. The fiber-SAP particle of claim 1, wherein the at least partially embedded fiber forms a fluid channels into an interior of the superabsorbent core particle and below an outer surface of the superabsorbent particle.

8. The fiber-SAP particle of claim 1, wherein an outer surface of the superabsorbent core particles is at least partially crosslinked.

9. The fiber-SAP particle of claim 1, wherein the fibers comprise microfibrillated cellulose fibers.

10. The fiber-SAP particle of claim 1, wherein the fibers comprise textile fibers.

11. The fiber-SAP particle of claim 1, wherein the fibers comprise hydrophilic fibers.

12. The fiber-SAP particle of claim 1, wherein the fibers comprise nanofibrillated cellulose fibers.

13. A fiber-SAP particle comprising:
a superabsorbent core particle; and
a plurality of fibers attached to the superabsorbent core particle, wherein at least one of the fibers is at least partially embedded into the superabsorbent core particle;
wherein the fibers are functionalized, the superabsorbent core particle is functionalized, or combinations thereof.

14. The fiber-SAP particle of claim 1, wherein the at least one fiber is embedded within a crevice of the superabsorbent core particle, and wherein the crevice is closed about the at least partially embedded fiber.

15. A fiber-SAP particle comprising:
a superabsorbent core particle; and
a plurality of fibers attached to the superabsorbent core particle, wherein at least one of the fibers is at least partially embedded into the superabsorbent core particel;
wherein the fiber-SAP particle is formed by wetting the fibers, dispersing the wetted fibers in a gaseous medium such that the wetted fibers are suspended in the gaseous medium, and mixing the wetted fibers suspended in the gaseous medium with the superabsorbent core particle such that the wetted fibers attach to the superabsorbent core particle, thereby forming the fiber-SAP particle.

16. The fiber-SAP particle of claim 15, wherein the wetting the fibers comprises providing a liquid suspension of the fibers in a liquid, and wherein the dispersing the wetted fibers comprises dispersing the liquid suspension.

17. The fiber-SAP particle of claim 16, wherein the dispersing the liquid suspension comprises forming an aerosol of the liquid suspension.

18. The fiber-SAP particle of claim 17, wherein forming the aerosol comprises spray drying the liquid suspension.

19. A fiber-SAP particle comprising:
a superabsorbent core particle; and
a plurality of fibers attached to the superabsorbent core particle;
wherein at least a portion of the fibers are embedded into the superabsorbent core particle such that the fibers extend through an outer surface of the superabsorbent core particle and into an interior of the superabsorbent core particle;
wherein the fibers comprise microfibrillated fibers, nanofibrillated fibers, or combinations thereof.

20. An absorbent article comprising:
an absorbent core composite comprising a substrate, a cover layer, and a plurality of fiber-SAP particles positioned between the substrate and the cover layer;
wherein each fiber-SAP particle comprises a superabsorbent core particle and a plurality of fibers attached to the superabsorbent core particle, and wherein at least one of the fibers is at least partially embedded into the superabsorbent core particle.

21. The article of claim 20, wherein adjacent fiber-SAP particles of the plurality of fiber-SAP particles are at least partially spaced apart.

22. The article of claim 21, wherein fibers of adjacent fiber-SAP particles of the plurality of fiber-SAP particles are entangled with one another.

23. The article of claim 22, wherein wicking paths are disposed between the adjacent, spaced apart fiber-SAP particles.

24. The article of claim 20, wherein the substrate and the cover layer each comprise a nonwoven.

25. The article of claim 20, further comprising a chassis, wherein the absorbent core composite is supported on the chassis.

26. The fiber-SAP particle of claim 1, wherein the plurality of fibers include fibers that are crosslinked with the superabsorbent particle, fibers that are crosslinked with other fibers of the plurality of fibers, or combinations thereof.

27. The fiber-SAP particle of claim 1, wherein the at least one fiber is in direct contact with the superabsorbent core particle.

28. The fiber-SAP particle of claim 1, wherein the at least one fiber is embedded within a crevice of the superabsorbent core particle with the superabsorbent core particle in an at least partially wetted state, and wherein the crevice is closed about the at least partially embedded fiber with the superabsorbent core particle in an at least partially dried state.

29. The fiber-SAP particle of claim 1, wherein the at least one fiber is embedded within a crevice of the superabsorbent core particle, and wherein the crevice is closed about the at least partially embedded fiber and entraps the at least partially embedded fiber.

30. A fiber-SAP particle comprising:
a superabsorbent particle having a plurality of crevices; and
a plurality of fibers attached to the superabsorbent particle and partially embedded into the crevices of the superabsorbent particle, wherein a first end of each fiber is positioned above an outer surface of the superabsorbent particle and a second end of each fiber penetrates into one of the crevices a distance below the outer surface of the superabsorbent particle and into an interior of the superabsorbent particle;
wherein the crevices entrap a portion of each fiber that is embedded therein; and
wherein the fiber-SAP particle is formed by a process comprising: wetting the superabsorbent particle to at least partially open the crevices; mixing the wetted superabsorbent particle with the fibers such that the fibers attach to the superabsorbent particle and are embedded in the at least partially open crevices; and drying the superabsorbent particle such that the crevices at least partially close and entrap the embedded fibers.

31. The fiber-SAP particle of claim 1, wherein the fibrillated fibers comprises microfibrillated fibers, nanofibrillated fibers, or combinations thereof.

32. The fiber-SAP particle of claim 1, wherein the fibrillated fibers comprise cellulose fibers.

* * * * *

UNITED STATES PATENT AND TRADEMARK OFFICE
CERTIFICATE OF CORRECTION

PATENT NO. : 12,239,748 B2
APPLICATION NO. : 17/307424
DATED : March 4, 2025
INVENTOR(S) : Andrew C. Wright and Eugenio G. Varona It is certified that error appears in the above-identified patent and that said Letters Patent is hereby corrected as shown below:

In the Claims

Column 25, Line 16, Claim 7, delete "channels" and insert --channel.--

Signed and Sealed this
Tenth Day of June, 2025

Coke Morgan Stewart
*Acting Director of the United States Patent and Trademark Office*